US006948918B2

(12) United States Patent
Hansen

(10) Patent No.: US 6,948,918 B2
(45) Date of Patent: Sep. 27, 2005

(54) MEMBRANE PUMP WITH STRETCHABLE PUMP MEMBRANE

(75) Inventor: Steffen Hansen, Hillerod (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/671,065

(22) Filed: Sep. 25, 2003

(65) Prior Publication Data

US 2004/0115068 A1 Jun. 17, 2004

Related U.S. Application Data

(60) Provisional application No. 60/416,856, filed on Oct. 8, 2002.

(30) Foreign Application Priority Data

Sep. 27, 2002 (EP) .............................. 02388066

(51) Int. Cl.$^7$ ................................................ F04B 43/06
(52) U.S. Cl. ....................................... 417/395; 604/153
(58) Field of Search .............................. 417/395, 383, 417/384, 385, 389; 137/859; 604/153

(56) References Cited

U.S. PATENT DOCUMENTS

| | | | | |
|---|---|---|---|---|
| 2,740,259 A | * | 4/1956 | Westlund | 417/395 |
| 2,980,032 A | | 4/1961 | Schneider et al. | |
| 3,176,712 A | * | 4/1965 | Ramsden | 137/859 |
| 4,265,600 A | | 5/1981 | Mandroian | 419/379 |
| 4,392,791 A | | 7/1983 | Mandroian | 417/379 |
| 5,149,413 A | | 9/1992 | Maget | 204/258 |
| 5,205,819 A | | 4/1993 | Ross et al. | 604/67 |
| 5,249,932 A | | 10/1993 | Van Bork | 417/386 |
| 5,520,523 A | | 5/1996 | Yorita et al. | 417/387 |
| 5,725,363 A | | 3/1998 | Bustgens et al. | 417/413.1 |
| 5,759,015 A | | 6/1998 | Van Lintel et al. | 417/322 |
| 2002/0123740 A1 | | 9/2002 | Flaherty et al. | 604/890.1 |

FOREIGN PATENT DOCUMENTS

| | | |
|---|---|---|
| DE | 26 24 129 A1 | 3/1977 |
| EP | 1 177 802 A1 | 2/2002 |
| WO | 98/01168 | 1/1998 |

OTHER PUBLICATIONS

Van Lintel H.T.G. et al., Sensors And Actuators A Physical, (1988) vol. 15, pp. 153–167.
Maillefer, Didier et al., Debiotec SA, (2001) pp. 413–417.

* cited by examiner

Primary Examiner—Michael Koczo, Jr.
(74) Attorney, Agent, or Firm—Marc A. Began, Esq.; Reza Green, Esq.; Richard W. Bosk, Esq.

(57) ABSTRACT

The invention relates to membrane pumps for delivering liquids. More specifically, a pump is provided having a pump housing with a pump cavity formed between first and second wall portions thereof, and an pump membrane pump membrane having first and second membrane surfaces arranged within the pump cavity, whereby a pump chamber is provided between the first wall portion and the first membrane surface, and an actuation chamber is provided between the second wall and the second membrane surface. Inlet means comprising an inlet valve in fluid communication with the pump chamber, and outlet means comprising an outlet valve in fluid communication with the pump chamber are provided. The pump membrane has a maximum volume position, and a drained volume position in which the first membrane surface in a stretched state abuts the first wall. To drive the membrane, actuating means for periodically shifting the pump membrane between the maximum volume position and the drained volume position is provided, thereby, in a situation of use, providing a flow of fluid.

31 Claims, 16 Drawing Sheets

MEMBRANE PUMP WITH STRETCHABLE PUMP MEMBRANE

CROSS-REFERENCE TO RELATED APPLICATIONS

This application claims priority under 35 U.S.C. 119 of European application no. EP 02388066.9 filed Sep. 27, 2002, and U.S. provisional application No. 60/416,856 filed Oct. 8, 2002, the contents of which are fully incorporated herein by reference.

FIELD OF THE INVENTION

The present invention relates to membrane pumps for delivering liquids. More specifically, the invention relates to micro membrane pumps suitable for pumping liquids as well as gasses, such pumps being suitable in particular for the in situ administration of medicinal drugs, the miniaturization of the pump allowing a user to carry the same on the body, or even to have the pump implanted directly in the body. Furthermore, such pumps can be used in areas such as biochemistry, microbiology, chemical analysis, and micro-reaction setups.

BACKGROUND OF THE INVENTION

Micropumps, i.e. pumps adapted for providing flow rates for liquids in the range of 1 $\mu$l/hour to 1 ml/min as such are well known in the art (although it should be noted that the indicated range is not per se a definition of a micropump). For example, an early micropump was proposed by H. van Lintel et al. in "A piezoelectric micropump based on micro-machining of silicon" (Sensors and Actuators, 15, 1988, pp. 153–157), the pump comprising a machined silicon plate placed between two glass plates and shifted by a piezoelectric element.

More specifically, the silicon plate is etched to form a cavity, which, with one of the glass plates, defines the pumping chamber, an inflow or suction valve and at least one outflow or expelling valve, allowing the pumping chamber to communicate respectively with an inflow channel and an outflow channel. The part of the plate forming a wall of the pumping chamber can be deformed by a control member provided for example as a piezoelectric element. The same is equipped with two electrodes which, when they are connected to a source of voltage, cause the deformation of the element and, consequently, the deformation of the plate, which causes a variation of the volume of the pumping chamber. This movable or deformable wall of the pumping chamber can thus be moved between two positions.

The functioning of the micropump is as follows. When no voltage is applied to the piezoelectric chip, the inlet and outlet valves are in their closed position. When a voltage is applied, an increase of the pressure inside the pumping chamber occurs, which causes the opening of the outlet valve. The fluid contained in the pumping chamber is then expelled through the outflow channel by the displacement of the deformable wall from a first position towards a second position. During this phase, the inlet valve is maintained closed by the pressure prevailing in the pumping chamber. Conversely, when the voltage is decreased, the pressure in the pumping chamber decreases. This causes the closing of the outlet valve and the opening of the inlet valve. The fluid is then sucked into the pumping chamber through the inflow channel, owing to the displacement of the deformable wall from the second position to the first position. As normally passive valves are used, the actual design of the valve will determine the sensitivity to external conditions (e.g. back pressure) as well as the opening and closing characteristics thereof, typically resulting in a compromise between the desire to have a low opening pressure and a minimum of backflow. As also appears, a membrane micropump functions as any conventional type of membrane pump, for example described for use as a fuel pump in U.S. Pat. No. 2,980,032.

One disadvantage with this type of micropump is that the silicon membrane's warping is slight in comparison with the size of the pump chamber, this making the pump less suitable for pumping of gas. Although the need for pumping gas as such may not be relevant in many fields of use, in many of the above-mentioned applications, it would be advantageous that the pumps be self-priming. To be able to draw in liquids in a pump initially filled only with air, a sufficiently high negative pressure must be generated when operating with air. Additionally, it may be required that the pumps also be self-filling, i.e. that no gas bubbles remain in the pump which would impair pump performance. Further, the manufacturing costs for silicon-based micropumps are very high, making this technology at present unsuitable for a disposable pump.

Addressing these problems, U.S. Pat. No. 5,725,363 (B. Büstgens et al.) discloses a micromembrane pump which comprises a lower housing, an upper housing and a pump membrane situated between them, with the membrane providing the inlet and outlet valve functions as well, operating together with the valve seat integrated with the housing. The pump membrane manufactured from polyimide is shifted by thermal expansion of a gaseous medium or by phase transition of a liquid medium to its gaseous state in the actuator chamber.

In the disclosed embodiment, a heating element is formed integrally with the pump membrane using a thin-layer-technology.

As indicated above, micropumps may be used in particular for the administration of medicinal drugs. It is therefore important that the flow rate of the micropump be well defined, so that the medical drug to be infused is metered very precisely. However, the above-described micropumps suffer in this respect, from certain imperfections.

More specifically, the flow rate of a micropump depends on the variation of the volume of the pumping chamber between the two end positions of the moving membrane. This variation of the volume depends on several parameters. For example, for a piezoelectric driven membrane the voltage applied to the piezoelectric element, the physical characteristics of the piezoelectric element (thickness, diameter, dielectric constant) and of the pump membrane (material, thickness) may influence the volume. Thus, the same voltage applied to micropumps apparently identical may cause differing deformations of the pumping chamber of these micropumps, which, subsequently, will produce differing flow rates. Correspondingly, for a heat driven pump, heat transfer through the pump membrane to the fluid to be pumped as well as to the surroundings will influence the accuracy of the pump. Furthermore, for a given micropump, the flow rate can drift in the course of time due to aging of the materials from which the piezoelectric chip is made and the aging of the adhesive used for its bonding. Finally, the flow rate of the micropump depends on the pressure in the outflow and inflow channels. Indeed, it would be possible to incorporate additional metering means, e.g. based on thermodilution as disclosed in EP 1 177 802 (Becton, Dickinson and Company).

Addressing these problems, U.S. Pat. No. 5,759,015 (H. van Lintel et al.) discloses a silicon based micropump incorporating first and second stopper members arranged in such a manner as to limit the amplitude of the movement of the pump membrane in its opposite directions, with the first stopper members limiting this movement during the sucking of the fluid inside the pumping chamber and the second stopper members limiting this movement during the expelling of fluid from the pumping chamber. Although the stopper members help to improve the accuracy of the pump, the movements of the pump membrane inherently relies on the manufacturing accuracy of both the stopper members and the wall portions which they abut. Based on this pump design, pumps have been developed which are described as self-priming (see for example D. Maillefer et al, "A high-performance silicon micropump for disposable drug delivery systems", Debiotec SA, Switzerland), however, as discussed above, a silicon based design still suffers from the disadvantage of high manufacturing costs.

A further problem with the silicon and polyimide based membrane pumps is the small stroke used in these pumps. For a metering pump this requires very fine tolerances which may be achieved using etching technologies, however, for moulded components it is difficult and/or expensive to ensure such fine tolerances.

Although the above-described micropump is capable of pumping gas as well as liquids and thus in principle is both self-filling, or self-priming, when connected to a reservoir comprising a fluid to be pumped, it is still left open how the pump should be operated to be primed in an efficient and controlled way when connected to a reservoir.

Having regard to the above discussion of known micropumps, it is an object of the present invention to provide a pump and components therefore which overcome one or more of the identified deficiencies and which can be manufactured in a cost-effective manner.

DISCLOSURE OF THE INVENTION

According to a first aspect of the invention, a pump device is provided having a pump housing with a pump cavity formed between first and second wall portions thereof, the first wall portion having a generally hollow configuration and the second wall portion having a generally raised configuration relative to the pump cavity, and a pump membrane having first and second membrane surfaces arranged within the pump cavity, such that a pump chamber is provided between the first wall portion and the first membrane surface, and an actuation chamber is provided between the second wall portion and the second membrane surface. Inlet and outlet means are provided in fluid communication with the pump chamber. The pump membrane has a maximum volume position in which the second membrane surface in a stretched state abuts and substantially conforms to the general configuration of the second wall portion, and a drained volume position in which the first membrane surface in a stretched state abuts and substantially conforms to the general configuration of the first wall portion.

By this arrangement a stretchable pump membrane can be shifted between well defined end positions, this providing a high metering accuracy for the pump yet allowing the pump to be manufactured cost-effectively. Indeed, it is here assumed that the pump is operated under conditions for which the pump has been designed, e.g. the pump is capable of overcoming the pumping resistance of the outflow means. Further, this arrangement provides a well-defined "resting" position allowing an inherently planar pump membrane to "rest" in a stretched state on the second wall portion; this providing a well defined maximum volume (or "start") position for the membrane. The membrane may be formed from a planar material or it may be formed with e.g. one or more dome-shaped membrane portions, the latter resulting in less stretching of the membrane when seated in its relaxed position as compared to the former.

To drive the pump membrane, the pump device is adapted to cooperate with actuating means for periodically shifting the pump membrane between the maximum volume position (typically corresponding to the end position for the "in-stroke" or "suction-stroke") and the drained volume position (typically corresponding to the end position for the "out-stroke" or "expelling-stroke"). In exemplary embodiments the actuating means is comprised in the pump device. Dependent upon the properties of the pump membrane, the pump membrane may be shifted to the maximum volume position by the actuating means, by elastic properties of the pump membrane, or a combination thereof.

The terms inlet and outlet means are meant to cover any structure and arrangement suitable for allowing a flow of fluid into and away from the pump chamber. In a basic form the in- and outlet means are merely in the form of openings, channels, conduits or the like which then may be connected to valve means which in combination with the above-described pump device may form a "complete" pump. Correspondingly, in exemplary embodiments, the in- and outlet means incorporate valve means which advantageously may be formed integrally with the pump housing and/or pump membrane.

As any material to a certain degree is flexible as well as stretchable, it should be noted that the term "stretchable" in the context of the present invention is used to denote a "positive" feature. The stretchability may be provided in different ways. For example, the pump membrane may be elastic in a "rubber-like" manner thereby allowing the pump membrane to abut and, in exemplary embodiments, to conform to the general configuration of the walls of the pump cavity. Alternatively, the pump membrane may have a corrugated or embossed configuration allowing it to be "pseudo-stretched", i.e. unfolded like e.g. the peripheral portion of a traditional loudspeaker membrane, the "stretching" relying on the flexibility of the membrane. For the latter configuration, the pump membrane as such may not be self-returning but would have to be shifted to the maximum volume position by the actuating means.

Indeed, the planar silicon and polyimide membranes of the known pumps inherently will be stretched to a small degree as they are forced to move (otherwise they were not able to move as they are fixed at their peripheral portions), however, these pump designs basically rely on the capability of the pump membrane being able to perform a stroke, i.e. to move up and downwards without conforming to the configuration of the opposed wall. Correspondingly, merely the flexibility properties of the pump membrane materials used are discussed in the above-cited documents.

Thus, by allowing the pump membrane to abut a well-defined structure of the pump chamber (i.e. the first wall portion) by simply stretching as it is forced by the actuation means towards its end position, a number of advantages are achieved. Basically, a stretchable membrane allows for a compact pump having large pump strokes and thereby excellent priming capabilities for expelling air contained in the pump chamber. Further, the stretching pump membrane provides a very simple means for achieving a high degree of metering accuracy, this in contrast to the elaborately formed stop means of the above-described known pump. In an exemplary embodiment, the pump membrane is formed from a sheet material having uniform thickness.

The first wall portion may have any configuration allowing the pump membrane to abut and, advantageously, conform thereto. The same considerations apply to the second wall portion.

For example, the first and second wall portions may have a generally smooth configuration such as generally concave respectively generally convex (as seen from the pump cavity) without any larger protrusions or depressions allowing a minimum of elastic deformation to take place within the pump membrane. The terms "generally concave" and "generally convex" are used to denote structures which may comprise planar portions as well as two or three dimensionally curved portions. For example, a generally concave or convex wall portion may be in the form of a portion of a sphere, may comprise both planar and curved portions (e.g. a planar central area and a curved circumferential portion), may be multifaceted without any curved portions. In other embodiments the wall portions may be in the form of a flat cone or a truncated cone. The wall portions may be rotationally symmetrical or may have a generally oval, square or oblong configuration, just as they may comprise areas which are raised or depressed relative to the surroundings. It should be noted that the examples given are not considered to be exhaustive.

The expression "to conform to the general configuration of the wall portion" does not imply that the entire surface area of the pump membrane has to be in contact with the abutting wall. In contrast, the wall and/or the membrane may be provided with a micro pattern preventing the membrane and housing surfaces from sticking to each other. In such a case less than half of the surface areas may be in direct contact with each other, however, as the pattern should be very fine, the spacing between the surfaces not in contact with each other will be so small, that variations in membrane position due to variations in actuation force will be negligible.

In exemplary embodiments the maximum stroke for the pump membrane (i.e. the maximum travel perpendicularly to the general plane of the pump membrane) is at least 0.10 mm. In other embodiments the maximum stroke is at least 0.20, 0.40 or 1.00 mm.

In exemplary embodiments, the actuation means for shifting the pump membrane is fluid pressure generating means comprising a conduit in fluid communication with the actuation chamber, this configuration allowing the pump membrane to rest on the second wall in its maximum volume (resting) position. When a drive fluid under pressure (relative to the pressure in the pump chamber) is supplied to the actuation chamber the pump membrane is shifted between the maximum volume position and the drained volume position. When the fluid pressure subsequently is lowered the pump membrane is shifted between the drained volume position and the maximum volume position, either by means of the elastic properties of the pump membrane or by applying a "suction pressure" in the actuation chamber. The drive fluid may be a liquid which is shifted back and forth by the pressure generating means (i.e. hydraulic drive), or it may be a gas. The driving gas pressure may be provided in any desirable way, e.g. by gas generation, gas pumping or gas expansion, and the gas pressure may be lowered by gas consumption, gas dumping, gas pumping or gas contraction.

For example, gas expansion and subsequent gas contraction can be provided by simply heating a fluid (gas or liquid) and subsequently cooling it by passive heat dissipation. Thus, in an exemplary embodiment, the actuation means for shifting the membrane comprises a fluid chamber in fluid communication with the actuation chamber, and heating means associated with the fluid chamber (e.g. arranged within or corresponding to the boundaries of the fluid chamber), this configuration allowing the pump membrane to rest on the second wall in its maximum volume (resting) position. In contrast, the heating element known from U.S. Pat. No. 5,725,363 is disposed directly on the pump membrane, which means that when fluids are delivered, greater heating capacity is required because of the markedly greater heat removal via the liquid to be pumped. Also, this leads to heating of the liquid which is particularly undesirable in some medical or biochemistry applications.

To further reduce heating of the liquid during pumping, the pump may be provided with a transmission cavity comprising a moveable transmission member arranged in the cavity, such that the transmission member divides the transmission cavity into an inlet chamber and an outlet chamber sealed from each other by the transmission member, the outlet chamber being in fluid communication with the actuation chamber, the inlet chamber being in fluid communication with a fluid chamber comprising heating means. Indeed, the larger the combined surface area of the different actuation cavities and connecting conduits is, the more heat will be lost during operation of the pump requiring a corresponding additional input of energy. In case the fluid to be pumped is heat resistant, the heating means may be formed on the pump membrane.

In alternative embodiments the actuating means are mechanical (e.g. a piezoelectric element arranged directly on the pump membrane or acting thereon via a transmission means, a solenoid or a motor-driven cam arrangement, or a pump for pumping air acting on the membrane) or electrostatic. Independently of the nature of the actuating means, the second wall portion, or a portion thereof, may be used as a piston for moving the pump membrane actively in either one or both directions.

The inlet and outlet valves may be of the passive type controlled by the flow of fluid resulting from movement of the pump membrane, or, alternatively, the inlet and outlet valves may be actively controlled. In the latter case the valves may be actuated by actuating means of the same type as the pump membrane or by a different type.

In order to allow for cost-effective manufacturing of a pump suitable for disposable use, the different cavities (e.g. pump cavity, fluid chamber, transmission cavity, valve housings, fluid communication conduits) may be formed between only two housing members, however, additional design considerations may call for use of more than two members. Correspondingly, a single membrane may be used to form the different membranes (e.g. pump membrane, valve membranes, transmission member) between opposed housing portions.

In a further way to reduce costs, a pump may be provided having interconnectable disposable and a durable portions, where the disposable portion comprises the fluid contacting elements (e.g. the pump cavity, the pump membrane, the inlet and outlet valves, and, if provided, a drug reservoir) whereas the durable portion comprises the actuating means and, in exemplary embodiments, control and energizing means for driving the actuation means. Alternatively, the actuating means may be included in the disposable portion, the durable portion comprising control and/or energizing means.

As discussed above, passive valves tend to be influenced by external conditions which indeed are undesirable. Thus, according to a second aspect of the invention a membrane valve is provided which advantageously can be incorporated in the above-described pump arrangements or used to control flow in general, the valve comprising a valve cavity formed generally between a wall portion and a valve seat portion, the valve seat portion having a generally convex configuration relative to the valve cavity, the valve seat portion comprising a fluid inlet. A valve membrane comprising a first valve membrane surface, a second valve membrane surface and a valve opening, is arranged within the valve cavity, a valve chamber being defined between the first membrane surface and the wall portion, the valve chamber comprising a fluid outlet. In this arrangement the valve membrane has a closed position in which the second valve membrane surface in a stretched state abuts and substantially conforms to the general configuration of the valve seat portion thereby closing the fluid inlet, and an open position in which the second valve membrane surface in a further stretched state is at least partially lifted away from the valve seat portion, thereby providing fluid communication between the fluid inlet and the fluid outlet via the valve opening.

In respect of the expressions "generally convex" and "to conform to the general configuration of the valve seat portion", the same considerations apply as for the pump membrane discussed above. To assure proper closing of the inlet opening, the valve membrane should be elastically self-returning.

To improve the opening characteristics of the valve, the inlet may be adapted to provide an initial lower flow resistance between the valve membrane and the valve seat surface surrounding the inlet such that the fluid can easily enter the space between the valve seat and the membrane and thereby generate the forces necessary to lift the membrane.

According to a third aspect of the invention a drug delivery device is provided, comprising a pump as described above, a reservoir for or containing a drug to be infused in fluid communication with the inlet means, the outlet means being adapted to cooperate with or comprising infusion means, control means for operating the pump and energizing means energizing the pump and control means. The infusion means may be in the form of a catheter tubing or transcutaneous access means such as an infusion needle, a flexible infusion cannula or a plurality of micro-penetrators. In an exemplary embodiment the reservoir is a prefilled, flexible reservoir.

In an exemplary embodiment the drug delivery device comprises a mounting surface adapted for application to the skin of a subject, the mounting surface advantageously comprising a pressure-sensitive adhesive allowing the device to be affixed to the skin of the subject user.

In an exemplary embodiment the outlet means comprises a hollow infusion needle communicating, in a situation of use, with the interior of the reservoir (i.e. via the pump), the infusion needle being moveable between a first position in which the pointed end of the needle is arranged in a retracted position relative to the mounting surface, and a second position in which a pointed distal end of the needle projects from the mounting surface.

In an embodiment the infusion needle is mounted on a pump assembly comprising the pump, the pump assembly being moveable (e.g. by rotation or linear movement) between a first position in which the pointed end of the needle is arranged in a retracted position relative to the mounting surface, and a second position in which the pointed end of the needle projects from the mounting surface.

Also the pump and the reservoir may be moveable relative to each other between a first position in which there is no fluid communication between the reservoir and the pump, and a second position in which fluid communication between the reservoir and the pump is established. In an exemplary embodiment movement of the reservoir, or a reservoir-containing component, between its first position and its second position results in movement of the pump assembly between the first and the second position thereof, for example by a ramp member associated with the reservoir and acting upon the pump assembly.

According to a fourth aspect of the invention, a membrane pump is provided allowing for controlled priming of an initially at least partially gas-filled pump with a liquid drawn from a reservoir comprising the liquid to be pumped. WO 98/01168 (Novo Nordisk A/S) discloses a dose setting device with a motor for driving a cartridge piston. By measuring the power consumption it is possible to detect whether air or liquid is forced out of the cartridge, this allowing a so-called air-shot to be performed, i.e. expelling air from a new cartridge or a new injection needle. As appears, this arrangement is based upon sensing the power input to the motor driving the piston, this in contrast to the present invention in which the pump action is based upon detection of the actual membrane movement, this allowing actuation means to be used which are operated in an on-off manner, i.e. the same amount of energy is used to energize the pump membrane for each actuation independently of the actual resistance against which the pump is operated.

Therefore, according to the fourth aspect of the present invention, controlled priming is performed by measuring a condition associated with membrane movement and detecting the differences which arise when the initially gas filled pump starts to pump liquid, i.e. the lower viscosity of gas results in a faster movement of the membrane during it pumping stroke, whereas the higher viscosity of the liquid drug will result in slower movement of the membrane. More specifically, a pump (of any given nature) is provided comprising means for operating the pump at a given priming cycle frequency, means for detecting a first pattern associated with the pumping of a gas or a mixture of gas and liquid, control means for continuing operation of the pump in accordance with the priming cycle frequency until a second pattern associated with the pumping of a liquid is detected, the control means terminating pump actuation in response thereto.

It readily appears that many different parameters will influence the movement of the pump membrane during the pumping of gas respectively liquid, e.g. pump membrane characteristics, valve characteristics, flow resistance in the inlet and outlet means, viscosity of the liquid to be pumped as well as the actual actuation force. It is therefore necessary for any given combination of a pump and a liquid to accurately optimize the pump membrane actuation force (or any other relevant parameter) in such a way that a readily identifiable difference will arise between membrane movements during the pumping of gas respectively liquid. For example, if the actuation force was very large compared to the pump resistance encountered during the pumping of liquid, this would result in very small differences which may be difficult to measure. For the actual measuring of the membrane movement, different parameters may be used, however it appears appropriate to measure parameters indicative of the time required for the "upstroke" movement, i.e. the stroke which actually drives out the gas or liquid from the pump chamber and through the outlet means. As the stroke distance of the pump membrane in most cases will be (much) larger than for the associated membrane valves, advantageously movement of the pump membrane is measured.

Membrane movement may be measured using any convenient means such as electrical contacts or electrical impedance measurement (resistance or capacitance) between electrical contacts/elements arranged on opposed surfaces of the pump membrane and the pump housing. However, membrane movement may also be detected indirectly e.g. by measuring the movement of mechanical actuation means such as a piston.

In an exemplary embodiment the priming means are provided in combination with a pump in accordance with the first aspect of the invention, however, the priming means may be used in combination with any type of membrane pump irrespective of the actuation means provided, e.g. piezoelectric or fluid actuation, or the type of the pump membrane used, e.g. flexible or stretchable.

A problem with existing drug delivery pumps is their ability to detect occlusions, especially when the pump is used for low flow applications. The problem is caused by the combination of low flow and compliance of the pump as it can take several hours for a blocked pump to build up enough pressure before the occlusion detector gives an alarm. Many traditional delivery pumps are compliant because the reservoir is part of the pump mechanism and/or because the fluid passage from the pump to the point of delivery (e.g. the distal end of an infusion needle) is compliant.

Using a membrane pump as a suction pump in a drug delivery device, a hydraulically much stiffer system can be achieved as the reservoir is "behind" the pump. Correspondingly, by also paying attention to the compliance of the outlet portion of the system a very stiff system may be provided such that an eventual occlusion will give an instant pressure increase, making it possible to alarm the user of an occlusion significantly faster than with normal pumps.

Correspondingly, in a further aspect of the invention a delivery device is provided comprising a pump device (e.g. as defined above), a reservoir adapted to contain a liquid drug and comprising an outlet means allowing the reservoir in a situation of use to be arranged in fluid communication with the inlet means of the pump device, pump outlet means (e.g. in the form of a hollow metallic needle comprising a pointed distal end portion adapted to be inserted though the skin of a subject), control means for operating the pump means to expel a drug from the reservoir and out through the outlet means, and energizing means for energizing the pump means and the control means. The delivery device further comprises indication means, as well as detecting means for detecting an occlusion condition associated with a pre-defined elevated pressure condition in the pump chamber during pump actuation, the detecting means being adapted to actuate the indication means when the occlusion condition is detected, wherein the outlet means is hydraulically rigid such that a partial or full occlusion of the outlet means will result in a substantially unrestricted pressure rise in the outlet means and thereby the pump chamber.

The occlusion condition associated with a pre-defined elevated pressure condition in the pump chamber may be selected from a large group of conditions. For example, the pressure in the pump chamber, in the outlet means or in gas or hydraulic actuation means may be directly measured. The occlusion condition may also be measured indirectly, e.g. by measuring the position or movement of the pump membrane, the valve membrane or of mechanical actuation means (e.g. these structures do not perform a full movement or does so slowly). Also current flow in electrically driven actuation means may be measured.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals (including peptides, proteins, and hormones), biologically derived or active agents, hormonal and gene based agents, nutritional formulas and other substances in both solid (dispensed) and liquid form. In the description of the exemplary embodiments reference will be made to the use of insulin. Correspondingly, the term "subcutaneous" infusion is meant to encompass any method of parenteral delivery to a subject.

BRIEF DESCRIPTION OF THE DRAWINGS

In the following the invention will be further described with references to the drawings, wherein.

In the figures like reference numerals are used to denote like or similar structures.

DESCRIPTION OF EXEMPLARY EMBODIMENTS

Figure 1A:
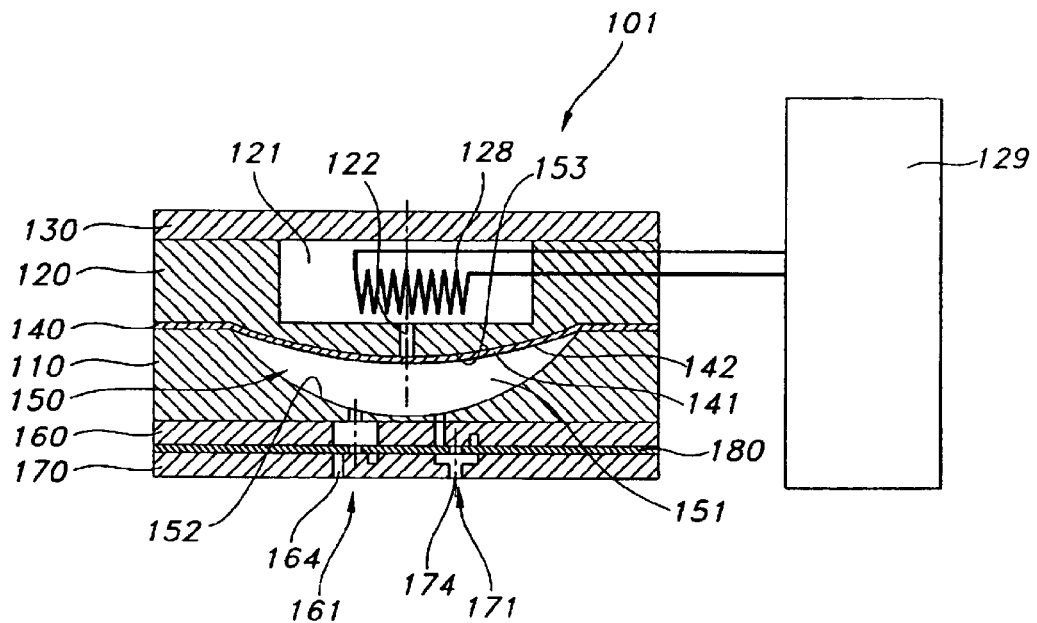
FIG. 1A shows in cross-section a schematic representation of a first embodiment of a pump in an initial state.

When in the following terms as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

More specifically, a pump 101 comprises a lower housing portion 110, an intermediate housing portion 120, an upper housing portion 130, an upper valve member 160 and a lower valve member 170. Between the lower and the intermediate housing portions an elastic pump membrane 140 is arranged and between the upper and lower valve members an elastic valve membrane 180 is arranged. Between the lower and the intermediate housing portions a pump cavity 150 is formed and between the upper and lower valve members inlet and outlet valve cavities for corresponding inlet and outlet valves 161, 171 are formed, the valves being in flow communication with the pump cavity and the exterior through openings formed in the lower housing portion and the lower valve member respectively. Between the intermediate and upper housing portions a fluid chamber 121 is formed.

The pump cavity is formed between a lower concave (seen from the cavity) wall portion 152 and an upper convex wall portion 153 together defining the boundaries for the pump cavity. The elastic membranes 140, 180 are generally hold in place between the lower and the intermediate housing portions respectively between the upper and lower valve members, however, corresponding to the pump cavity and the valve cavities, the membranes can move and forms here a pump membrane 141 respectively valve membranes, the latter having holes 162, 172. The pump membrane, having a lower surface 142 and an upper surface 143, divides the pump cavity in a lower pump chamber 151 defined between the lower wall 152 and the lower membrane surface 142, and an upper actuation chamber 154 defined between the upper wall 153 and the upper membrane surface 143. As appears, in the illustrated "resting" or "initial" state of the pump, the pump membrane conforms to the general convex configuration of the upper wall portion, the actuation chamber thereby being fully collapsed whereas the pump chamber has its maximum volume; correspondingly, the pump membrane is in its "maximum volume position".

The pump membrane may be inherently planar such that it "rests" in a stretched state on the convex wall portion; this providing a well defined maximum "start" volume position for the pump membrane.

In the valve membranes openings are formed which provide for valving action as the holes can be closed by cooperation with valve seats 163, 173 formed in the valve cavities, whenever there is excess pressure on the side of the membrane opposite the valve seat. Oppositely, if the pressure on the membrane on the side of the valve seat exceeds the pressure on the opposite side, the membrane is lifted off the valve seat and the hole in the membrane is no longer blocked so that fluid can flow there through. Fluid is drawn to the inlet valve through inlet opening 164 and further to the pump chamber through a pump chamber inlet opening. From the pump chamber fluid is pumped to the outlet valve through a pump chamber outlet opening and further to the outlet opening 174.

The tightness of the valves in their closed positions depends to a great extent on the amount of coverage, the surface roughness of the valve membrane and the valve seat and very much on the flexibility of the membrane. If the membrane is very thin, proper sealing may be achieved even under unclean conditions since the membranes would then be in a position to bend around small particles, such as crystals contained in, for example, some types of insulin preparations. The opening and closing behaviour of the valves can be influenced by the height of the valve seat, e.g. the membrane mounting surface and the valve seat may be arranged in the same plane or the valve seat may be raised so that the membrane is deflected upwardly in its rest position. Since the membrane is tensioned with this arrangement, a certain pressure difference is required to open such a valve.

The above examples illustrate that a number of design parameters can be varied to achieve the desired valve characteristics such as back flow and operating pressure which again may be chosen in accordance with the operating cycle frequency of the pump. A valve design which advantageously can be used in combination with a pump device as described in the present application is described with reference to FIGS. 12 and 13.

The pump is actuated by actuation means which in the shown embodiment is by thermal expansion of a fluid disposed in the fluid chamber 121 when heated by a heating structure 128 disposed within the chamber, the fluid chamber being in fluid communication with the actuation chamber through a fluid conduit 122 formed in the intermediate housing portion. The heating structure may be arranged in the cavity space as shown or on a wall portion.

The different housing portions and the membrane are bonded or held together in a sandwich assembly by any convenient means establishing the necessary sealing between the different elements, e.g. sonic welding, laser bonding or by using adhesives.

Figure 1B:
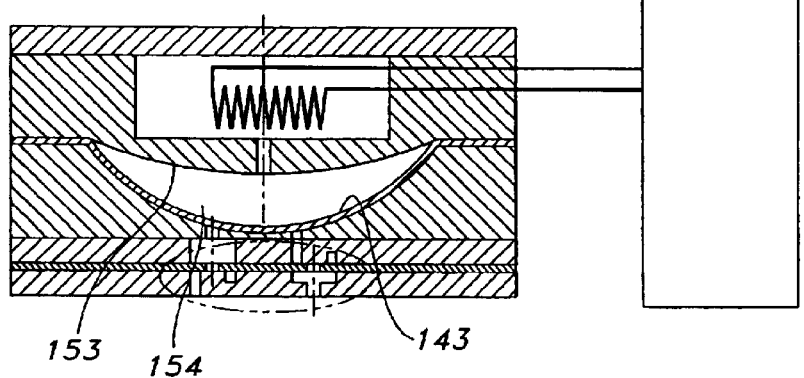
FIG. 1B shows in cross-section a schematic representation of the first embodiment in an actuated state.
Figure 1C:
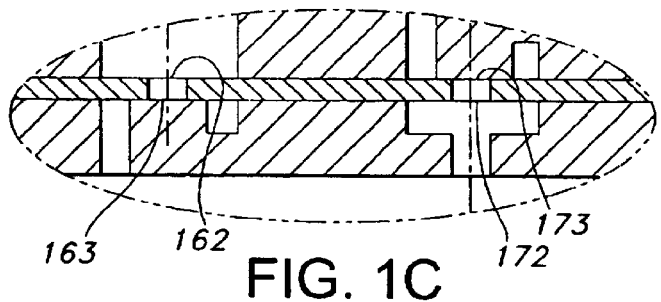
FIG. 1C shows a detail of the valve arrangement of FIG. 1A.

FIG. 1B discloses the same pump as described with reference to FIG. 1A, the difference being that the pump membrane has been activated by the actuation means. As appears, in the illustrated "activated" state of the pump, the pump chamber is fully collapsed whereas the actuation chamber has its maximum volume; correspondingly, the pump membrane is in its "drained volume position".

In operation of the pump, the heating structure 128 is energized by a short current pulse supplied by control means 129 and is thereby heated. The heat is transferred to the fluid medium (which may be a gas, a fluid or a mixture thereof; in the shown embodiment air is used) in the fluid chamber 121 whereby the resulting pressure increase results in expansion of the heated gas (air) through the fluid conduit 122 and into the initially collapsed actuation chamber 154. The pressure and volume increase in the actuation chamber resulting from the temperature increase deflects the pump membrane 140 downwardly to its stretched "drained volume position" in conforming abutment with the lower wall 152 thereby driving out the medium to be pumped (a gas, liquid or a mixture thereof) contained therein. Indeed, it is here assumed that the pump is operated under conditions for which the pump has been designed, e.g. the pump is capable of overcoming the pumping resistance of the outflow means.

The resulting pressure increase of the medium to be pumped is transmitted, via the flow passages, to the valves whereby, in the area of the inlet valve, the valve membrane 162 abuts the valve seat 163 and closes the valve whereas, in the area of the outlet valve, the membrane 163 is lifted off the valve seat 173 thereby freeing the opening in the valve membrane through which the pump medium is then discharged.

After termination of the current pulse, the medium in the actuation chamber 154 and in the fluid chamber 121 starts to cool down by heat transfer and heat radiation. If the medium in the actuation chamber is a gas, its pressure and, as a result, the volume of the actuation chamber is reduced thereby; if the medium is a liquid, the vapours will condense and the original conditions will be re-instated. As a result, the stretched pump membrane resumes its original "maximum volume position" and, because the medium to be pumped was driven out of the pumping chamber, a vacuum is now generated in the pump chamber 151 and at the inlet valve 160. In accordance with the valve operation described above, the outlet valve closes ad the inlet valve opens and the medium to be pumped is sucked into the pump chamber. This process is repeated with each pumping cycle.

Figure 2A:
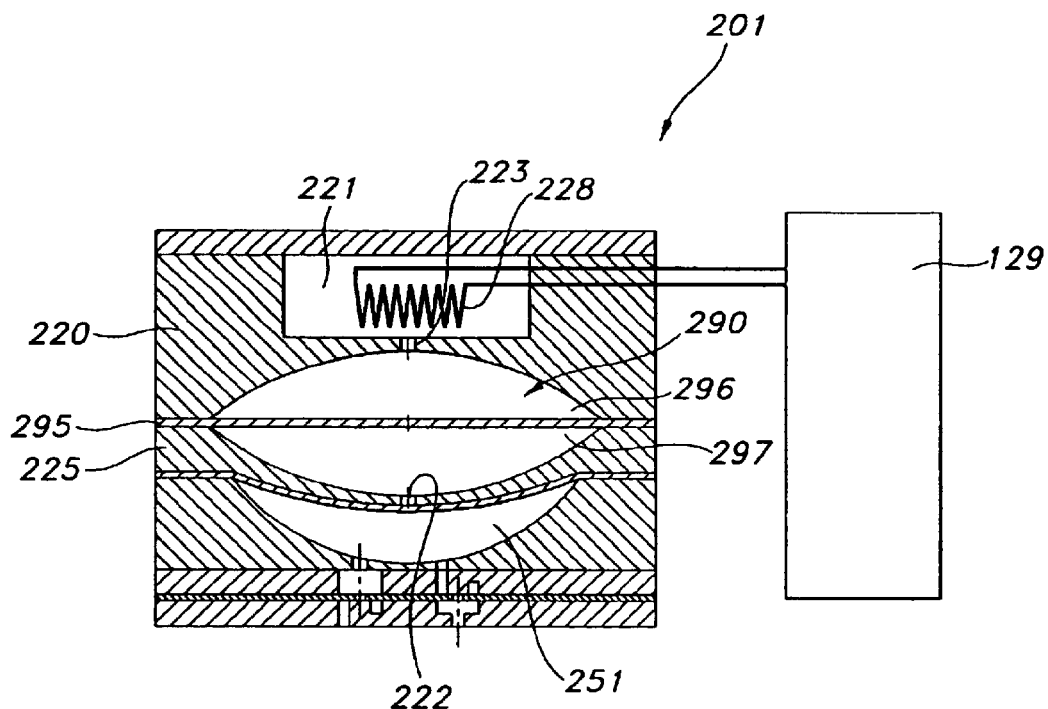
FIG. 2A shows in cross-section a schematic representation of a second embodiment of a pump in an initial state.
Figure 2B:
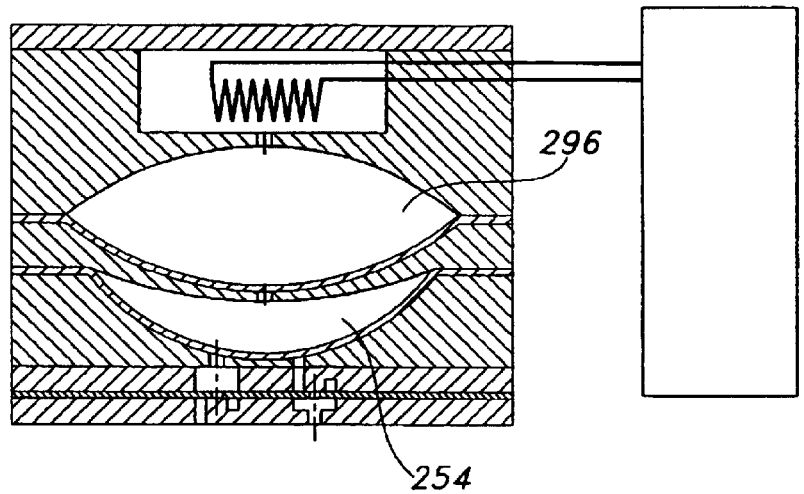
FIG. 2B shows in cross-section a schematic representation of the second embodiment in an actuated state.

Next, with reference to FIGS. 2A and 2B, a second embodiment of a pump 201 comprising a transmission cavity with a transmission membrane will be described.

In respect of the pump "as such" (i.e. the pump chamber, valves, fluid chamber and heating structure) the second embodiment corresponds in general to the first embodiment, however, the pump 201 comprises first and second intermediate housing portions 220, 225 instead of the single intermediate housing portion 120. A transmission cavity 290 is formed between concave wall portions 291, 292 of the first respective the second intermediate housing portions which in combination define the boundaries for the transmission cavity. Arranged between the first and second intermediate housing portions an elastic membrane forms a transmission membrane 295 dividing the transmission cavity in an upper inlet chamber 296 and a lower outlet chamber 297 sealed from each other by the transmission membrane. In the shown embodiment the inlet chamber has an initial positive volume, however, it other configurations it may be fully collapsed in its initial or resting position (just as the actuation chamber). The inlet chamber is in fluid communication with the fluid chamber 221 through conduit 223 formed in the intermediate housing portion, and the outlet chamber is in fluid communication with the actuation chamber 254 through conduit 222.

As regards the pump and valves per se, the second embodiment of the pump operates in the same way as the first embodiment, the operating differences being in regard of the transmission chamber. More specifically, when heated by the heating structure 228 the expanding fluid (here: air) in the fluid chamber expands through the conduit 223 to the inlet chamber 296. As the inlet chamber expands the transmission membrane 295 is deflected downwardly to its "actuated position" in abutment with the lower wall (see FIG. 2B). The fluid (here: gas) thus expelled from the outlet chamber is forced through the conduit 222 to the actuation chamber 254 thereby deflecting the pump membrane 241 and driving out the medium contained in the pump chamber 251.

Figure 3A:
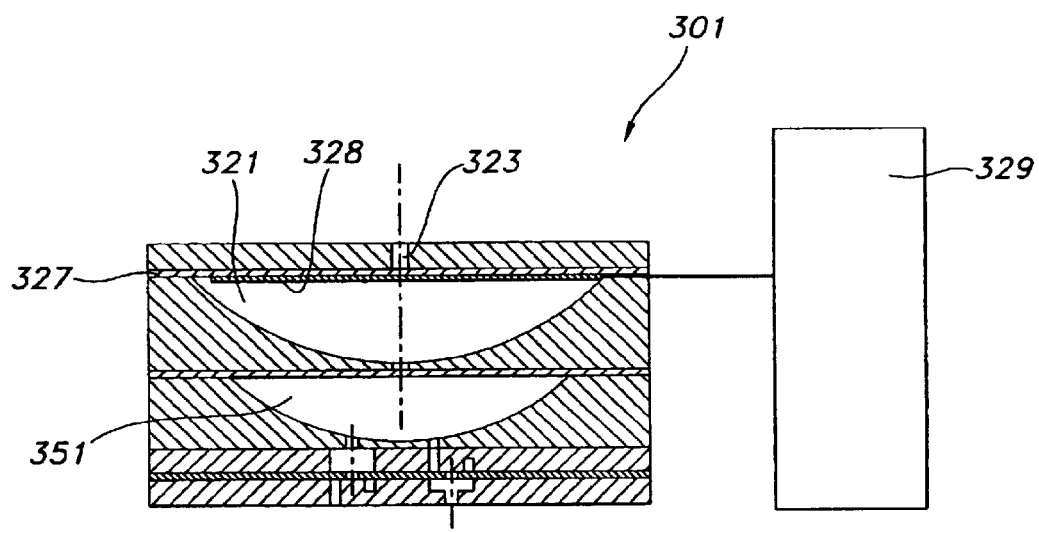
FIG. 3A shows in cross-section a schematic representation of a third embodiment of a pump in an initial state.

Next, with reference to FIGS. 3A and 3B, a third embodiment of a pump 301 will be described.

In respect of the pump "as such" (i.e. the pump chamber, valves, and fluid chamber) the third embodiment corresponds in general to the first embodiment, however, there are two differences. Firstly, the upper wall portion 353 defining the upper boundary for the pump cavity is substantially planar, the pump membrane thereby resting thereon in an un-stretched state. Secondly, the pump fluid is displaced from the pump chamber 321 by means of an actuator membrane 327 arranged between the upper and intermediate housing portions 330, 320. Corresponding to the fluid chamber the actuator membrane is provided with a disc-formed piezoelectric element 328 which can be shifted between a first generally planar configuration and a second downwardly curved configuration by control means 329.

The third embodiment may be provided either as an integral unit comprising both cavities, or as a system comprising a pump unit and an actuation unit adapted to be operatively connected to each other, the interface between the two units being arranged corresponding to intermediate housing portion 320 and the pump membrane.

Figure 3B:
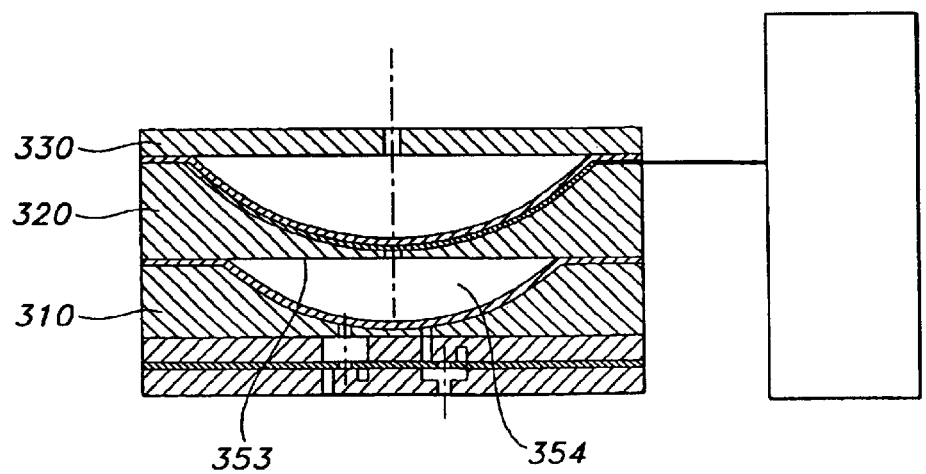
FIG. 3B shows in cross-section a schematic representation of the third embodiment in an actuated state.

In operation of the pump, the piezoelectric element is energized by a short current pulse supplied by control means 329 whereby the actuator membrane is shifted from its first to its second position thereby driving out fluid (here: air) from the fluid cavity thereby deflecting the pump membrane downwardly as in the first embodiment (see FIG. 3B). In order to allow the drive membrane to move, a vent 323 is provided behind the membrane.

Figure 4A:
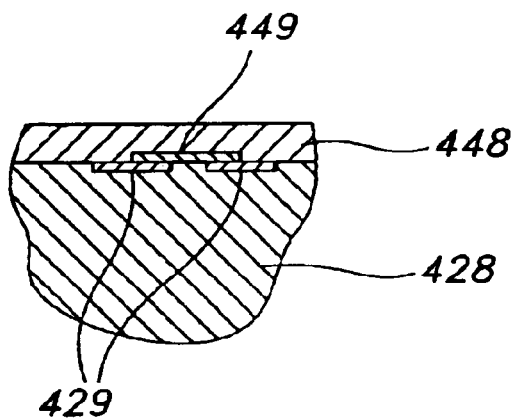
FIG. 4A shows in detail capacitor/contact means arranged on a pump membrane and housing portion.

FIG. 4A shows a portion of a pump membrane 448 in resting abutment with an opposed planar wall portion 428 (in contrast to the above-described embodiments, the pump membrane has a "lower" resting position). As appears, on the lower surface of the pump membrane is formed an electrical capacitor area 449 and on the upper surface of the wall portion is formed a pair of electrical capacitor areas 429, which is connected by electrical paths (not shown) formed on the corresponding housing portion for communication with membrane movement detecting circuitry (not shown). For illustrative purposes the contact areas are shown as formed into the opposed surfaces, however, normally the contact areas and associated paths are very thin and are formed directly onto the surfaces. Using capacitive detecting circuitry the contact is less critical just as the contacts are arranged outside the flow path thereby eliminating any influence of fluid between the contacts.

Figure 4B:
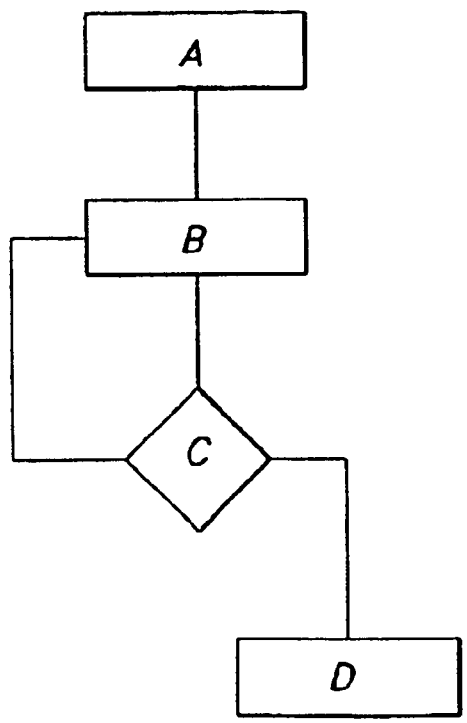
FIG. 4B shows a flow chart illustrating the sequence of operations carried during a priming cycle.

FIG. 4B shows a flow chart illustrating the sequence of operations carried out by controlling means when operating a pump comprising membrane position detecting means during a priming cycle. The priming cycle is started whereby the pump is actuated in accordance with a predetermined priming cycle frequency (A), and a first pattern of movement of the pump membrane associated with the pumping of a gas or a mixture of gas and liquid is detected (B). The detected membrane movement pattern is compared with a second predetermined pattern associated with the pumping of a liquid (C). In case the two patterns are within a pre-specified range, the priming cycle is ended (D). In case the two patterns are not within the pre-specified range, the priming cycle continuous. In case the second pattern is not identified within a given pre-defined period, a malfunction condition is identified. The term "pattern of movement" merely indicates that a value associated with pump membrane movement is identified.

Instead of comparing the detected pattern/value with a preset pattern/value, it would also be possible to operate the pump until a steady state was achieved, i.e. the pattern/values for a pre-defined number of operations vary within only a pre-defined range.

Figure 5:
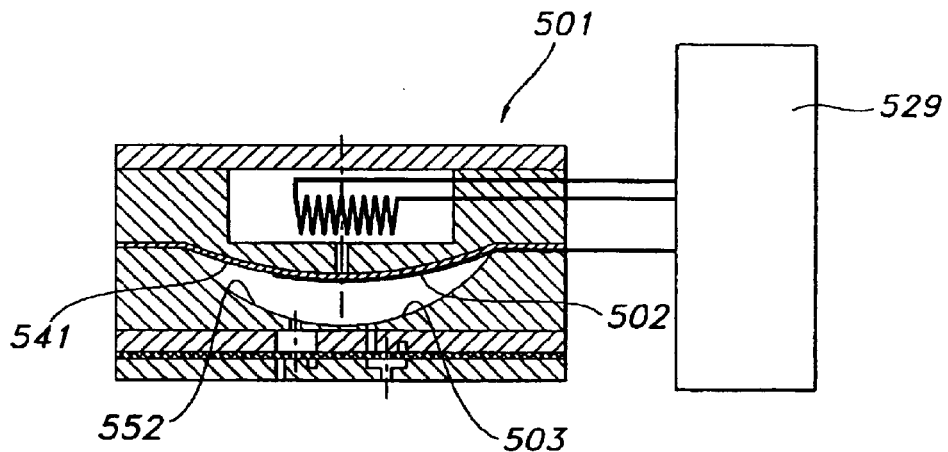
FIG. 5 shows in cross-section a schematic representation of a fourth embodiment of a pump in an initial state.

With reference to FIG. 5, a fourth embodiment of a pump 501 will be described, the pump essentially corresponding to the first embodiment, however, on the opposed facing surfaces of the pump membrane 541 and the lower concave wall portion 552 conductive means are arranged. More specifically, the pump membrane comprises a pair of "active" electrodes 502 electrically connected to control and detecting means 529 and the wall portion comprises an "inactive" electrode 503. As the electrodes are arranged on the "wet" side of the pump membrane, the electrodes are advantageously formed as capacitor members having a relatively large surface area.

Figure 6:
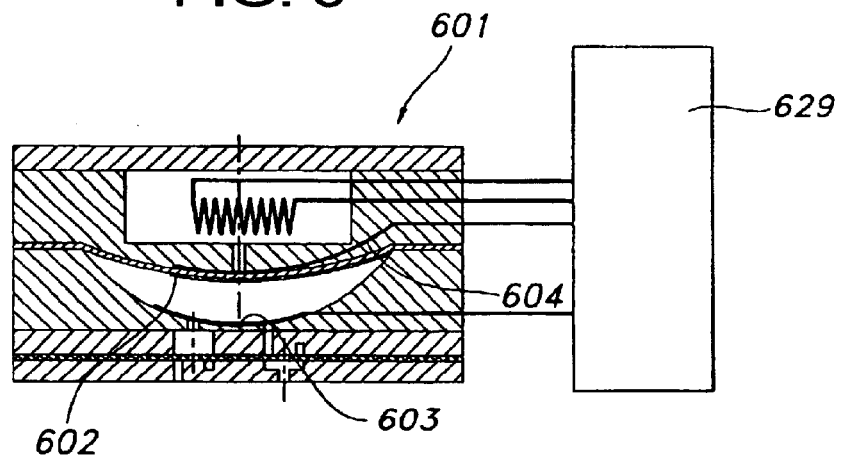
FIG. 6 shows in cross-section a schematic representation of a fifth embodiment of a pump in an initial state.
Figure 7:
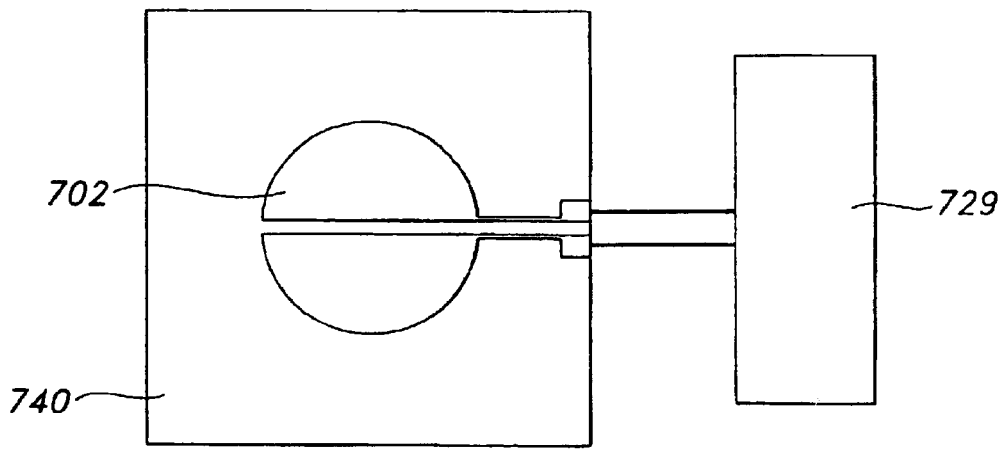
FIG. 7 shows a configuration for an electrode.

With reference to FIG. 6, a fifth embodiment of a pump 601 will be described, the pump essentially corresponding to the forth embodiment, however, the pump membrane comprises a passive electrode 602 whereas each of the opposed pump cavity walls are provided with a pair of "active" electrodes 603, 604 connected to the control means. In this way it will be possible to detect movement of the pump membrane relative to both of the wall portions providing improved control. The active electrodes 702, arranged either on the pump membrane 740 or a housing wall, may be configured as shown in FIG. 7, whereas the passive electrodes may be formed as a single disc-formed area, however, numerous configurations for the electrodes would be possible depending on the type of electrodes and the configuration of the control and detecting means.

Next, with reference to FIGS. 8A–8H, a sixth embodiment comprising a transmission cavity with a transmission member will be described.

More specifically, a pump 801 comprises an upper housing portion 810, a lower housing portion 820 and a PCB (printed circuit board) member 830. Between the upper and lower housing portions an elastic membrane 840 is arranged, and between the lower housing portion and the PCB member a sealing membrane 880 is arranged. Between the PCB member and the lower housing portion a fluid chamber 821 is formed, and between the lower and upper housing portions a pump cavity 850, a transmission cavity 890 as well as inlet and outlet conduits associated with corresponding inlet and outlet valve housings for corresponding inlet and outlet valves 861, 871 are formed.

As described with respect to the first embodiment, the pump cavity is formed between an upper convex (seen from the cavity) wall portion 852 and a lower concave wall portion 853 together defining the boundaries for the pump cavity, just as the elastic membrane 840 arranged between the upper and lower housing portions corresponding to the pump cavity and the valve cavities forms the pump membrane 841 respectively the valve membranes. The pump membrane thus divides the pump cavity in a lower pump chamber and an upper actuation chamber.

The transmission cavity 890 is formed between a lower planar wall portion 822 and an upper concave wall portion 812 together defining the boundaries for the transmission cavity. The interposed elastic membrane 840 forms a transmission membrane 895 dividing the transmission cavity in a lower inlet chamber 896 and an upper outlet chamber 897 sealed from each other by the transmission membrane. In the shown embodiment the inlet chamber is fully collapsed in its initial or resting position Oust as the actuation chamber), see FIG. 8E. The inlet chamber is in fluid communication with the fluid chamber 821 through conduit 823 formed in the lower housing portion 820, and the outlet chamber is in fluid communication with the actuation chamber through conduit 822. In the areas of the inlet valve 861 and of the outlet valve 871, holes 862, 872 are formed in the membrane 840, which provide for valving action as the holes can be closed by cooperation with valve seats 863, 873. Fluid is drawn to the inlet valve through inlet opening 864 and further to the pump chamber. From the pump chamber fluid is pumped to the outlet valve and further to outlet opening 874.

The fluid chamber 821 is formed between a recessed portion 824 in the lower surface of the lower housing portion 820 and an upper surface portion of the PCB member 830. As appears, the sealing membrane 880 comprises a cut-out portion 881 arranged in register with the recessed portion, the sealing member merely serving to seal to the contacting portions of the PCB and the lower housing portion. Indeed, in a different design it would be possible to dispense with the sealing member. The heating structure is in the form of a printed circuit trace 828 provided on the PCB member corresponding to the fluid cavity. The trace may be manufactured using thin-film technology. In the shown embodiment the circuit trace is provided with contacts 829 to be arranged externally on the assembled pump (see FIG. 8C), however, it would be possible to mount energizing as well as control means directly on the PCB within the confinement of the pump housing, e.g. in a cavity (not shown) formed between the PCB member and the lower housing portion. Also cordless transmission means may be provided integrally with the pump housing. As appears, in register with the recessed portion 824 the lower housing portion is provided with an upper recessed portion 827 which reduces heat take up from the heating structure during actuation of the pump just as it improves heat dissipation from the fluid chamber during cooling.

The different housing portions, the membranes and the PCB member are bonded or held together in a sandwich assembly (see FIG. 8C) by any convenient means establishing the necessary sealing between the different elements, e.g. sonic welding, laser bonding or using adhesives.

Figure 8A:
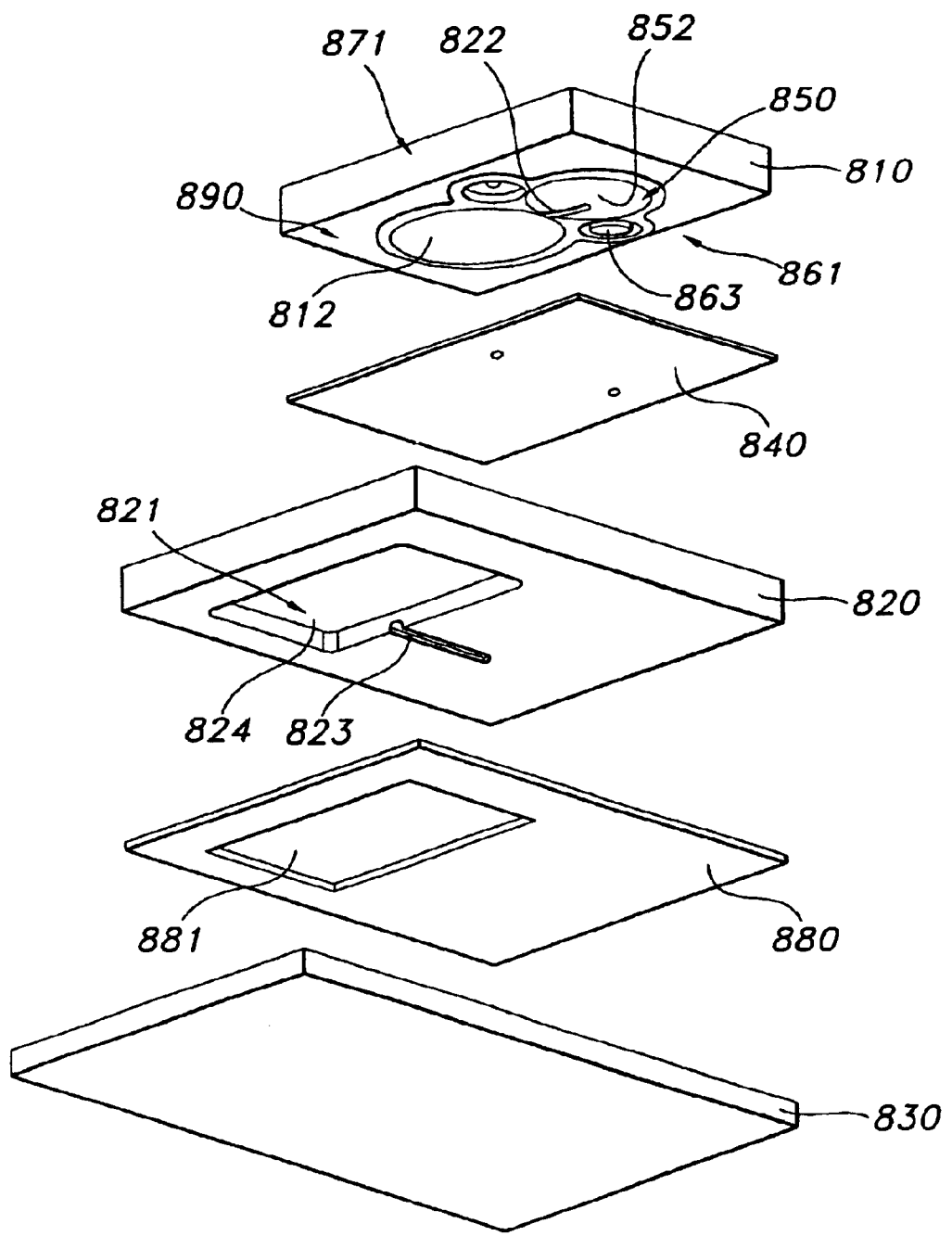
FIG. 8A shows an exploded view of a sixth embodiment of a pump seen from below.
Figure 8B:
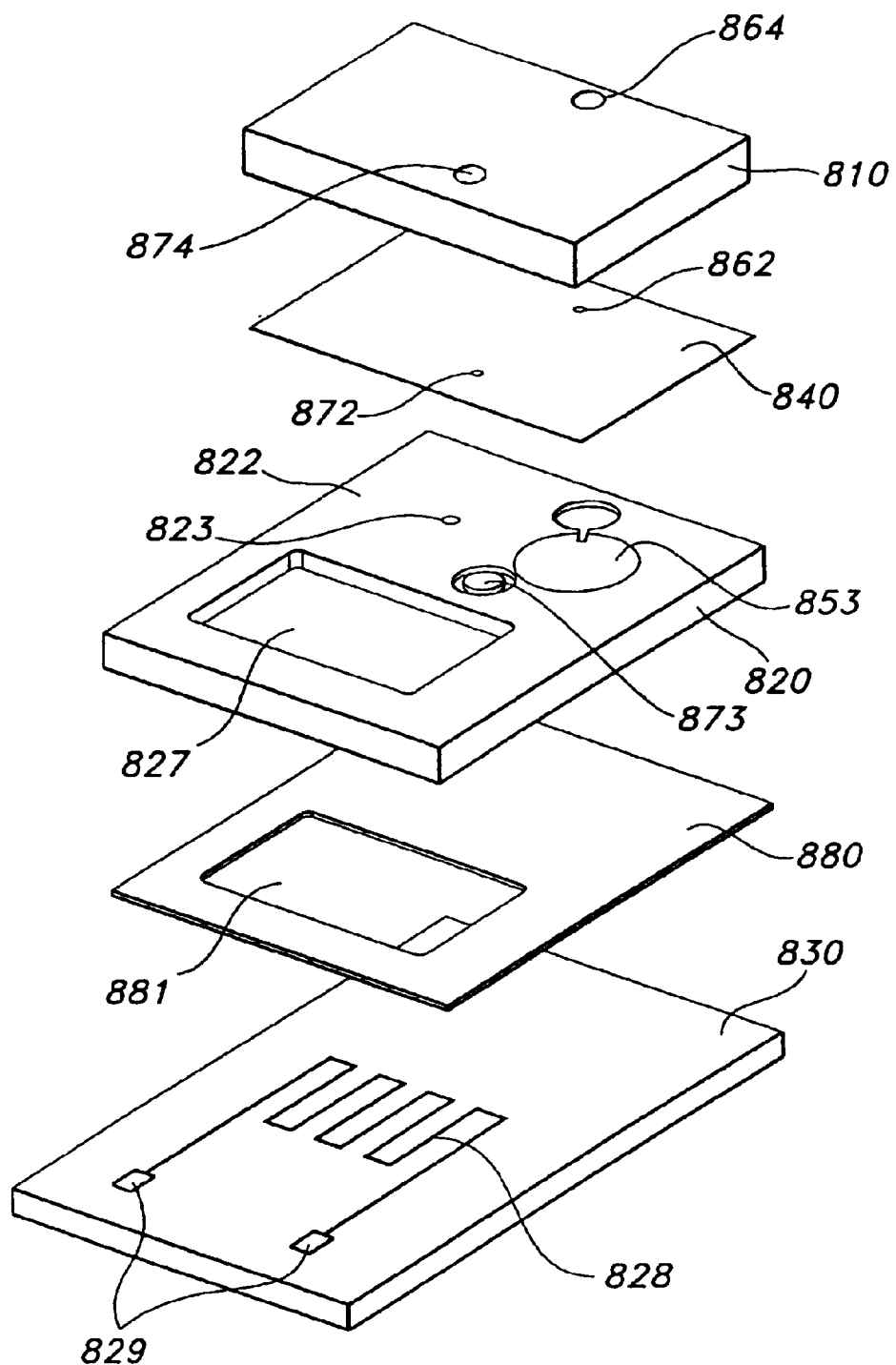
FIG. 8B shows an exploded view of the sixth embodiment seen from above.
Figure 8C:
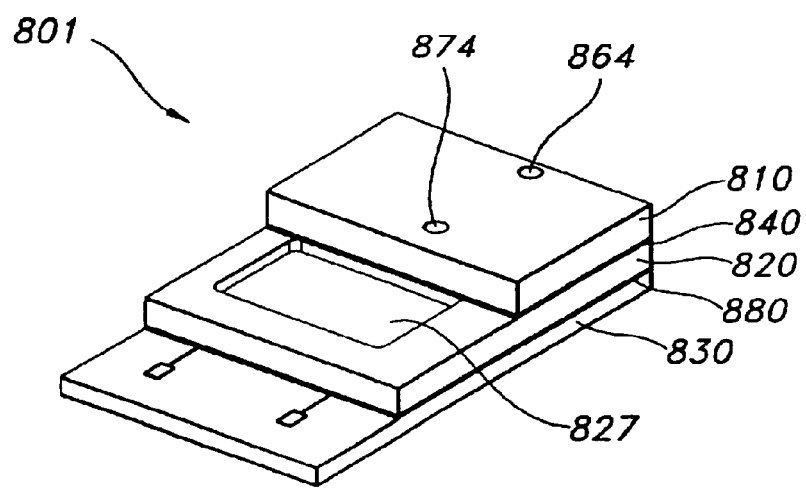
FIG. 8C shows the sixth embodiment in its assembled state.
Figure 8D:
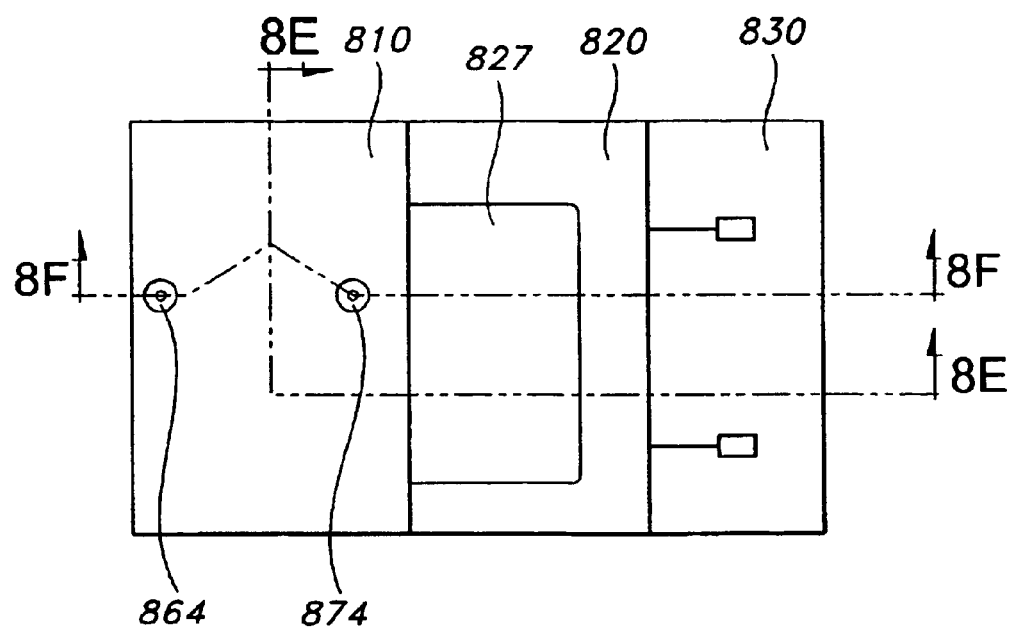
FIG. 8D shows the sixth embodiment seen from above with lines E—E and F—F indicated.
Figure 8E:
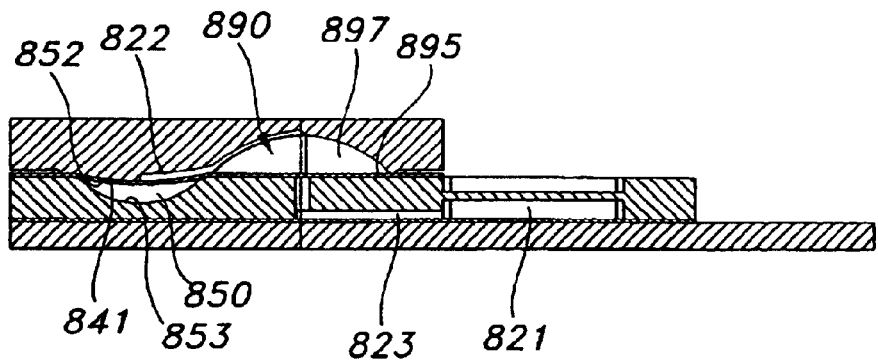
FIGS. 8E and 8F show cross-sections along the lines E—E and F—F respectively of the pump in an initial state.
Figure 8F:
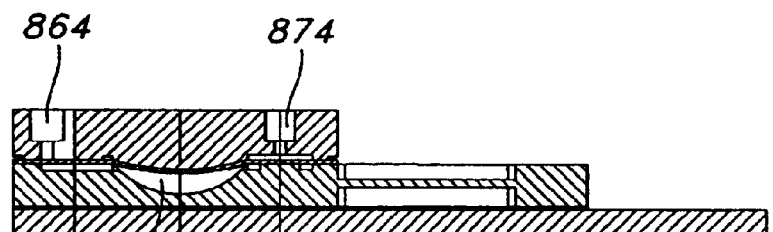
Figure 8G:
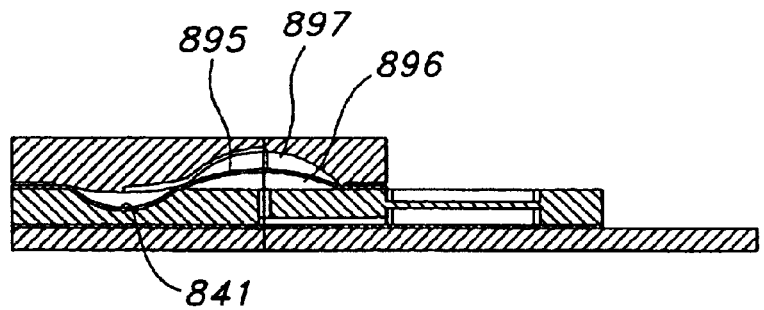
FIGS. 8G and 8H show cross-sections along the lines E—E and F—F respectively of the pump in an actuated state.
Figure 8H:
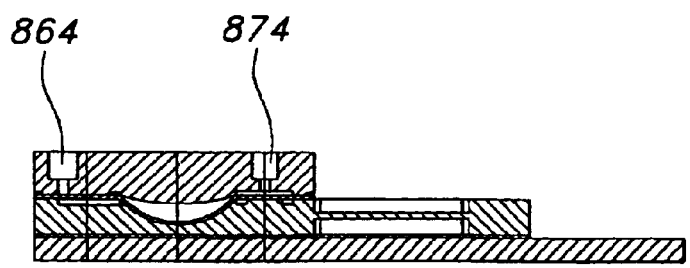

As regards the pump and valves per se, the sixth embodiment of the pump operates in the same way as the second embodiment, the operating differences being in regard of the transmission chamber. More specifically, as shown in FIGS. 8F–8H, the inlet chamber 896 is fully collapsed in an initial state, whereas the outlet chamber 897 is not fully collapsed in the actuated state. Further, the conduits leading to a from the transmission chamber are longer just as in the shown orientation the transmission membrane is deflected upwardly to its actuated position.

The housing portions may be formed from any suitable material, e.g. plastics such as PMMA or polycarbonate (PC). Depending on the intended use, the pump-, valve- and transmission-membranes may be formed from any suitable elastic material such as rubber, TPE (thermoplastic elastomer) or polyurethane.

Examples: For use in an insulin infusion pump the pump chamber is dimensioned after a lowest basal rate of 0.5 IU/hour divided in 2 portions. This gives a pump chamber volume of 0.25 IU which for U200 insulin corresponds to 1.25 µl which can be realized in a pump chamber defined between spherical caps having a diameter of 3.58 mm and heights of 0.49 mm respectively 0.25 mm. The valves had dome shaped valve seats with a diameter of 3.00 mm and a dome height of 0.1 mm for the inlet valve and 0.2–0.35 mm for the outlet valve. For corresponding prototypes plane polyisoprene rubber membranes having a thickness of 70 µm were used. Also moulded (e.g. comprising dome-shaped membrane portions) silicone rubber membranes were used. For a piston actuated pump as shown in FIG. 8M a piston with a diameter of 2.7 mm was used in a pump chamber having a diameter of 3.0 mm.

In the above-described embodiments, an actuation chamber has been provided between the pump membrane and a fixed wall portion, the membrane being actuated by a fluid forced into the chamber. In alternative arrangements, the wall portion may be moveable in which case it during the different stages of the pump cycle may be in full or partial contact with the pump membrane. Further, a transmission means may be arranged between the moveable wall portion and the pump membrane.

Figure 8K:
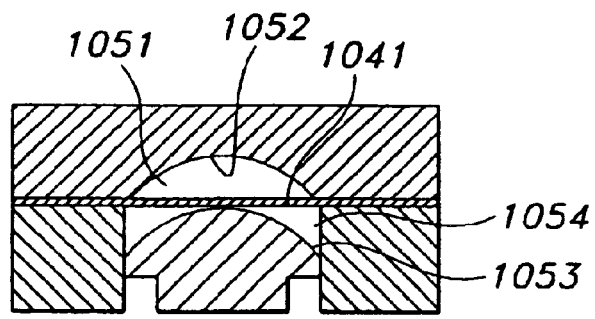
FIGS. 8K–8M show embodiments having moveable wall portions.

Correspondingly, FIG. 8K shows an embodiment in which a pump chamber 1051 is provided between a fixed first wall portion 1052 and a stretchable pump membrane 1041, and a vented actuation chamber 1054 is provided between the pump membrane and a second wall portion formed by an upper surface 1053 of a piston member 1050 having substantially the same configuration as the first wall portion. When the piston is moved upwardly by associated drive means (not shown) the pump membrane is shifted from the maximum volume position to the drained volume position. As the first wall portion substantially corresponds to the second wall portion, the pump membrane is forced into contact with the latter. As appears, in contrast to the above-described embodiments, the volume of the actuation chamber decreases during actuation.

Figure 8L:
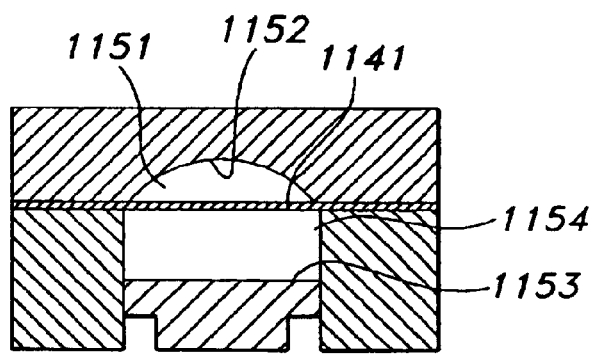
Figure 8M:
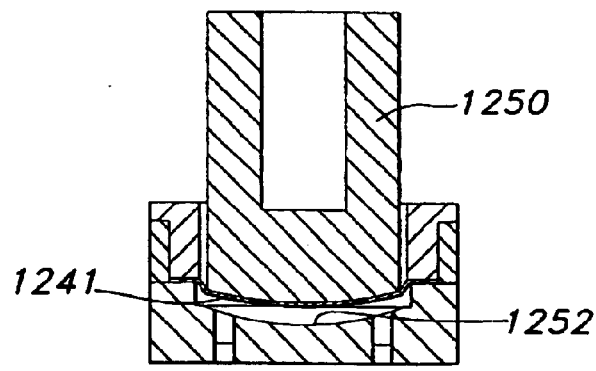

FIG. 8L shows an embodiment in which a pump chamber 1151 is provided between a fixed first wall portion 1152 and the pump membrane 1141, and an actuation chamber 1054 is provided between the pump membrane and a second wall portion formed by an upper surface 1153 of a piston member 1150. The actuation chamber is filled with a substantially non-compressible fluid. When the piston is moved upwardly by associated drive means (not shown) the pump membrane is shifted from the maximum volume position to the drained volume position. As the pump membrane is shifted towards the first wall portion by the fluid, the membrane will conform to the first wall portion. As appears, in contrast to the above-described embodiments, the volume of the actuation chamber remains constant.

FIG. 8M shows a further alternative configuration of a piston-actuated membrane pump in which a piston 1250 in the maximum volume position is in substantially full contact with a stretched pump membrane 1241. However, in contrast to the embodiments of FIGS. 8K and 8L the stroke volume is determined by the stroke of the piston such that the pump membrane in the drained volume position does not come into contact with the first wall portion 1152. To improve clarity, the inlet and outlet means are not shown in FIGS. 8K–M.

In the embodiments described with reference to FIGS. 1–8, the actuation means has been based on active gas expansion by heating and gas contraction by passive heat dissipation, however, as also discussed in the introductory portion, many different means can be applied in order to provide a flow of fluid to the actuation chamber through the fluid conduit to thereby shift the pump membrane from the maximum volume position to the drained volume position, and many different means can be applied for controlling a flow of fluid from the actuation chamber through the fluid conduit to thereby shift the pump membrane from the drained volume position to the maximum volume position.

For example, a gas may be supplied to gas pumping means controlling the flow of gas to the actuation chamber. The gas pumping means may an electrically controlled electrochemical motor as disclosed in U.S. Pat. No. 5,149,413 (hereby incorporated by reference) which can either be used to pump gas in both directions or be used as a one-way gas pump in combination with a dump valve. The gas may be supplied from a storage reservoir (as shown in U.S. Pat. No. 5,149,413) or it may alternatively be generated by e.g. electrolytic action. In a further alternative configuration, gas generation may be used to directly raise the pressure in the actuation chamber, in which case the gas pressure may be lowered by means of a dump valve or by controlled combustion.

Figure 10:
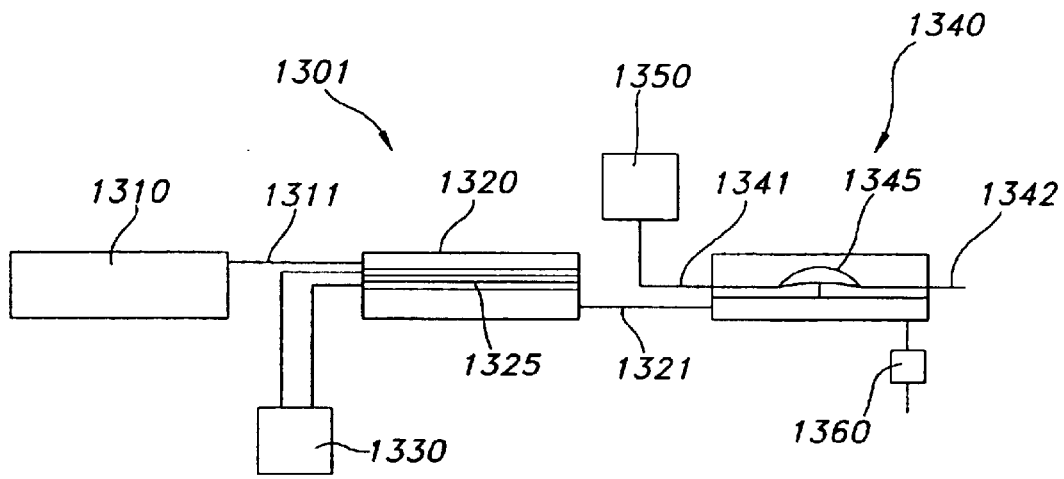
FIG. 10 shows a drug delivery device comprising an electrochemical motor.

FIG. 10 illustrates schematically an embodiment of a drug delivery device 1301 comprising a gas supplying means 1310 for either storing or generating a gas, an electrochemical motor 1320 comprising an electrolytic membrane arrangement 1325 capable of pumping a gas by applying a voltage across the membrane, the voltage being controlled by control means 1330 (a detailed disclosure of the working principles of an electrolytic membrane can be found in U.S. Pat. No. 5,149,413), and a membrane pump 1340 with a pump cavity 1345 as described above (for illustrative purposes is the valves not shown), the pump comprising an outlet 1342 and an inlet 1341 in fluid communication with a drug reservoir 1350. The delivery device further comprises conduits 1311, 1321 providing fluid communication between the gas supplying means and the electrochemical motor, and between the electrochemical motor and the membrane pump. In a situation of use the electrochemical motor is controlled to pump gas back and forth across the membrane thereby shifting the pump membrane of the pump. Alternatively, the electrochemical motor is used only to generate pressure and a dump valve 1360 is provided by means of which the pressure in the actuation chamber of the pump can be lowered, this allowing an elastic pump membrane to revert to its resting state. If gas is generated swiftly, the dump valve may be of a passive, permanently leaking type.

As appears from the above, the shown membrane pumps comprise membrane inlet and outlet valves. The inlet valve's function is to open during the suction stroke and close during the pump stroke. Because of the very limited force during the suction stroke this valve should be soft i.e. open for very low pressures in the open direction. The outlet valve's function is to close during the suction stroke and open during the pump stroke.

Figure 11:
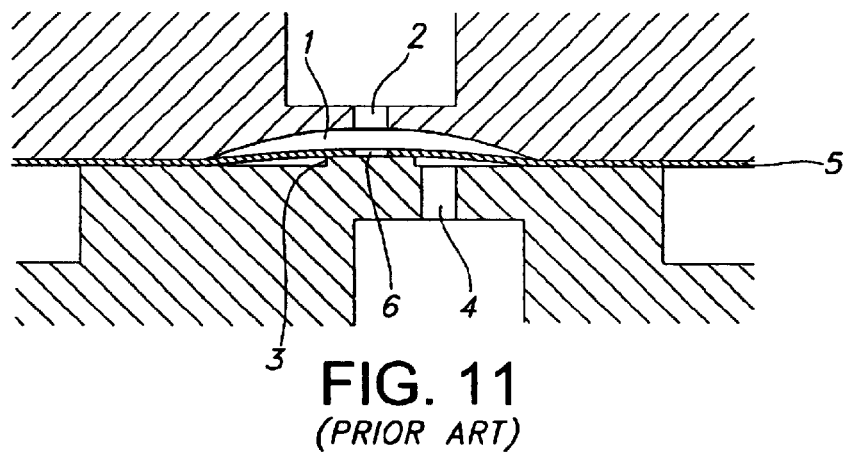
FIG. 11 shows an embodiment of a valve.

FIG. 11 shows a prior art valve type which was investigated during development of the present invention. The valve is a one way check valve with a valve cavity 1, an inlet 4, an outlet 2, an elevated valve seat 3 covered by a membrane 5 with a hole 6 in it. When pressure on the inlet side is raised the membrane is lifted away from the seat allowing a flow through the valve. If pressure is put on the outlet side, the membrane will sit even harder on the seat allowing no flow through the valve. The valve seat is elevated to give the valve a pretension. This is to ensure that the valve is tight at low pressures, and that the valve will open for flow in the open direction only if the pressure exceeds a certain level. This is to avoid free flow through the pump when the pump is not running. This valve type however was rejected after it became obvious that it made the pump back pressure dependent. This was tested on a pneumatically actuated membrane pump, where the pump chamber itself was truly volumetric without any back pressure dependence. It is the hypothesis of the present inventors that the problem was related to the membrane area not supported by the valve seat.

Figure 12:
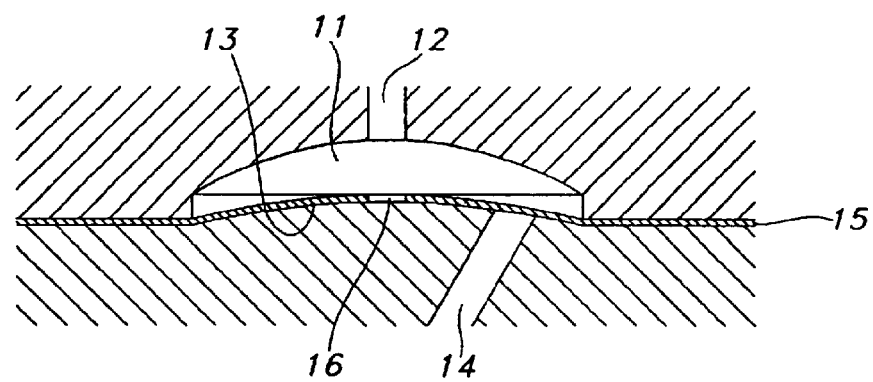
FIG. 12 shows a further embodiment of a valve.
Figure 13A:
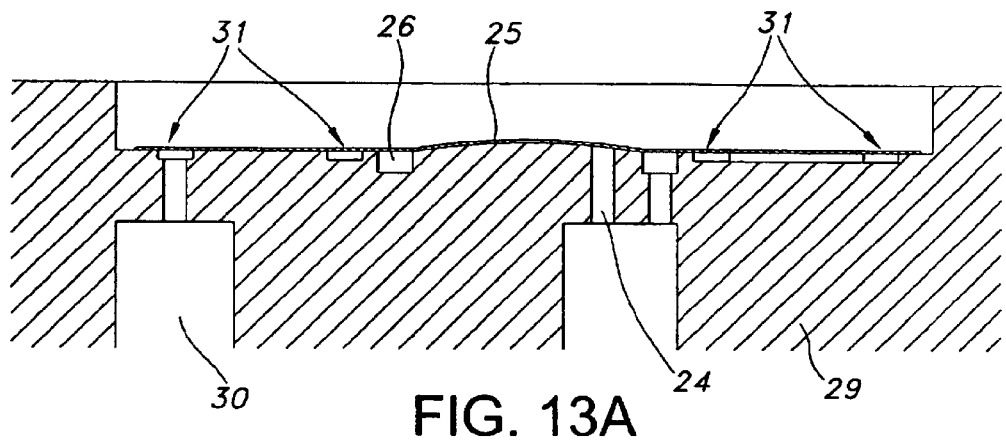
FIGS. 13A–13C shows an arrangement for mounting a valve membrane.

To address this problem a valve with a dome shaped valve seat 13 an inlet 14 and an outlet 12 was designed where a valve membrane 15 with an opening 16 is fully supported by the dome shaped valve seat as shown in FIG. 12. During testing it was found that pump output was low with the prior art valve presumably because some of the stroke volume goes to deflection of the soft valve membranes. It was also found that counter pressure sensitivity was higher for the prior art valve. In contrast, the better performance of the dome valve is probably due to the fact that the perfectly stiff valve with no unsupported, flexible membrane portions eliminates sponginess in the system.

In order to make reproducible valves of the kind described here it is crucial to be able to control and reproduce the membrane tension. The main problem is that when a rubber membrane is clamped between two surfaces some material is squeezed out into the valve cavity.

Figure 13B:
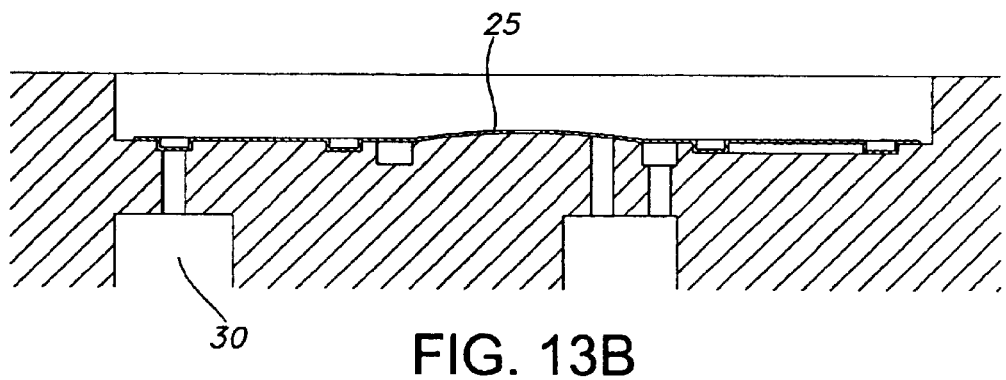
Figure 13C:
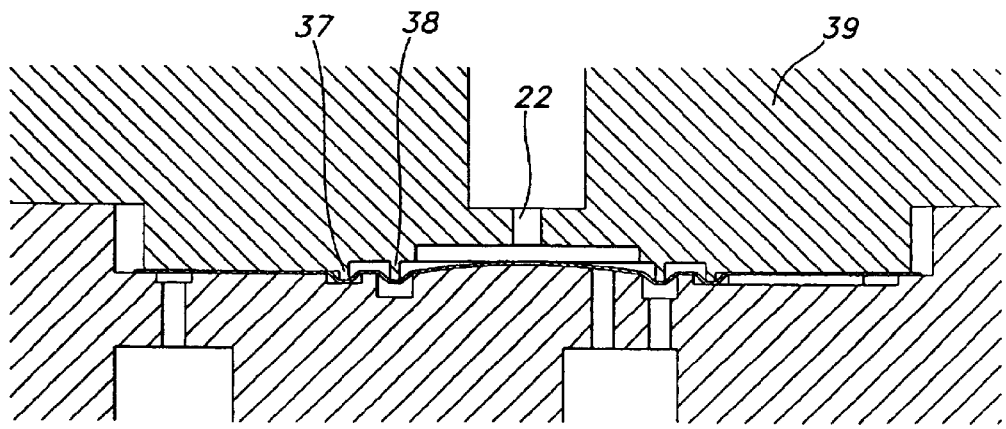

If a fairly flat diaphragm (or membrane) is considered, its tension is extremely sensitive to material moving inwards from the clamped edge portions. To avoid this, a special clamping system was developed. First, a membrane 25 was placed over a lower valve seat member 29 without any tension (FIG. 13A), the valve seat member comprising an inlet 24 a vacuum connection 30 in fluid communication with vacuum grooves 31, and a fixation groove 26. Then the membrane was held with vacuum in the grooves (FIG. 13B). Lastly, the membrane was clamped with an upper valve member 39 with an outlet 22 and a set of narrow mounting rings 37, 38 adapted to engage corresponding grooves in the lower member thereby fixating the membrane between the two valve members, where after the vacuum was released (FIG. 13C). When the membrane is held with vacuum it is stretched a "little bit" more than what is squeezed away by the clamping ring resulting in a clamped membrane with close to zero tension.

With this system it was possible to make reproducible valve characteristics using a polyisoprene membrane over a PMMA seat.

Although the above-described design provided very good laboratory results, it may not be necessary to use this design in production. For example, it is believed that the same control of the membrane tension can be achieved by a moulded membrane held in place by its geometry.

The above shown valves were dimensioned to open at 1 mBar for the inlet valve and 20 mBar for the outlet valve using this formula for large diaphragm deflections:

$$\frac{pr^4}{Et^4} = K_1 \frac{y}{t} + K_2 \left(\frac{y}{t}\right)^3$$

Where:
p=pressure difference over the membrane.
r=radius of the membrane.
t=thickness of the membrane.
y=deflection of the membrane.
E=Young's modulus.

In order to provide (almost) completely tight valves, it was found that very smooth surface finish should be used for the valve seats as well as the membranes. It was further found that in order to improve "opening" of the valve, the area around the inlet opening (either the valve seat or the valve membrane) could advantageously be provided with a fine surface pattern (or a less smooth surface) such that the fluid could easily enter the space between the valve seat and the membrane and thereby generate the forces necessary to lift the membrane.

With reference to FIGS. 9A–9E a drug infusion device suitable for incorporating one or more aspects of the present invention will be described.

More specifically, a drug infusion device 901 comprises a base plate 910, a first cover member 920 and a second cover member 930, the three elements in combination forming a housing in which a pump assembly 940 and a flexible drug reservoir 950 are arranged.

The base plate comprises a lower generally planar surface 918 adapted to be mounted in engagement with a skin-surface of a user, and an upper surface 919 provided with connecting means allowing the first and second cover members as well as a pump assembly 940 to be mounted on the base plate. More specifically, the base plate comprises three upstanding hook-members 911 adapted to engage corresponding hook structures 921 on the first cover member to thereby lock the two members to each other in a snap-action manner, as well as a pair of parallelly arranged opposed members 912 having outwardly open grooves adapted to engage corresponding flange structures 931 on the second cover member allowing the two members to be mounted in sliding engagement with each other. In order to control movement between the two members, the grooves and the flanges may be provided with corresponding ratchet or locking means 916, 932. To help align the second cover member as it is moved towards the first cover member, the base plate comprises a ridge member 913 adapted to engage a corresponding groove structure 933 on the second cover member. The base plate member further comprises an aperture 914, a part-cylindrical "female" hinge member 915 adapted to engage the pump assembly, as well as an opening 917 associated with the hinge member.

The pump assembly 940 comprises a membrane pump as well as control means, actuating means (e.g. heating means), contact means and an energy source for driving the pump. The pump assembly is configured with a (part) cylindrical hinge body 941 from which protrudes a pump body 942 wherein the pump and driving means are arranged. On the lower surface of the hinge body an engagement member 947 is arranged. The pump inlet is in fluid communication with an inlet needle 943 protruding axially from an end of the hinge body and the pump outlet is in fluid communication with an infusion needle 944 protruding from a lower surface 948 of the pump body, both needles having a pointed free end. The hinge body is adapted to be pivotally received in the hinge member 915 with the engagement member 947 arranged in the opening 917 to prevent axial displacement of the pump assembly, and with the infusion needle in alignment with the aperture 914.

The flexible reservoir 950 is in the form of a pouch- or bag-like member formed from a pliable material and provided with a needle penetratable connecting means, e.g. a self-sealing septum (not shown). The reservoir is easily collapsible allowing the drug contained therein to be sucked out by the pump without the need for additional venting means. The reservoir is mounted and hold in place under the second cover member by appropriate means. In the shown embodiment the reservoir is prefilled with a drug such as insulin, however, the reservoir may also be adapted to be filled by the user prior to user.

The above-described components are assembled in two subassemblies (see FIGS. 9C and 9D), a main assembly 960 and a reservoir assembly 970, this allowing the assemblies to be sterilized independently if necessary. More specifically, the main assembly comprises the base plate member with the first housing member mounted on top thereof providing a cavity in which the pump assembly 940 is pivotally arranged in the hinge member 915, and the reservoir assembly comprises the second housing member with the reservoir mounted corresponding to a lower surface thereof. The hinge may be configured to provide an upwardly biasing force preventing the pump assembly from pivoting downwardly. The second housing member is provided with an end portion having a grooved area 934 and an oppositely arranged shroud portion 935 adapted to slide under the first cover member, as well as a lower ramp member 936 associated with the lower surface of the second housing member, the function of which will be explained in greater detail below.

Figure 9A:
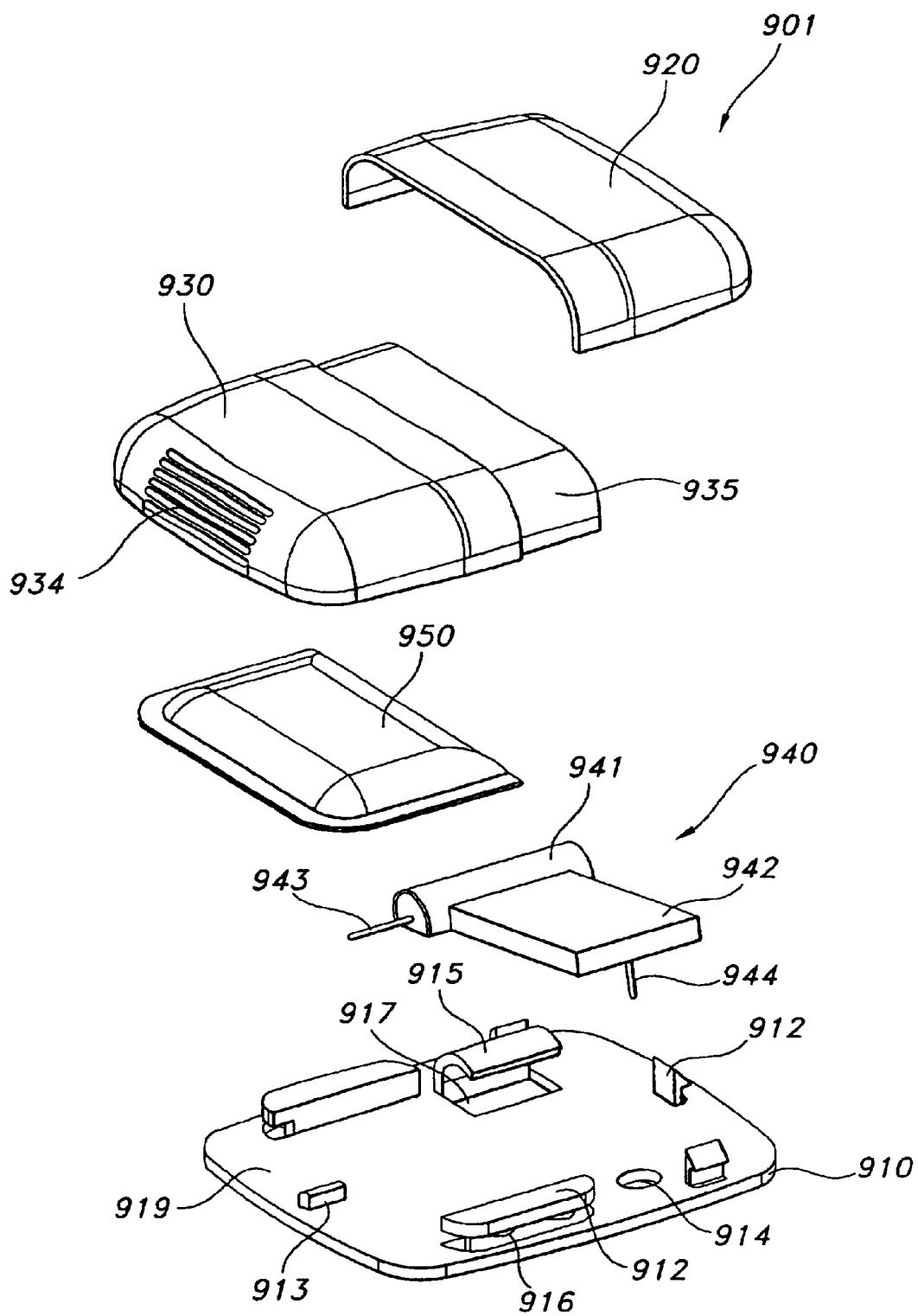
FIG. 9A shows an exploded view of a drug infusion device seen from above.
Figure 9B:
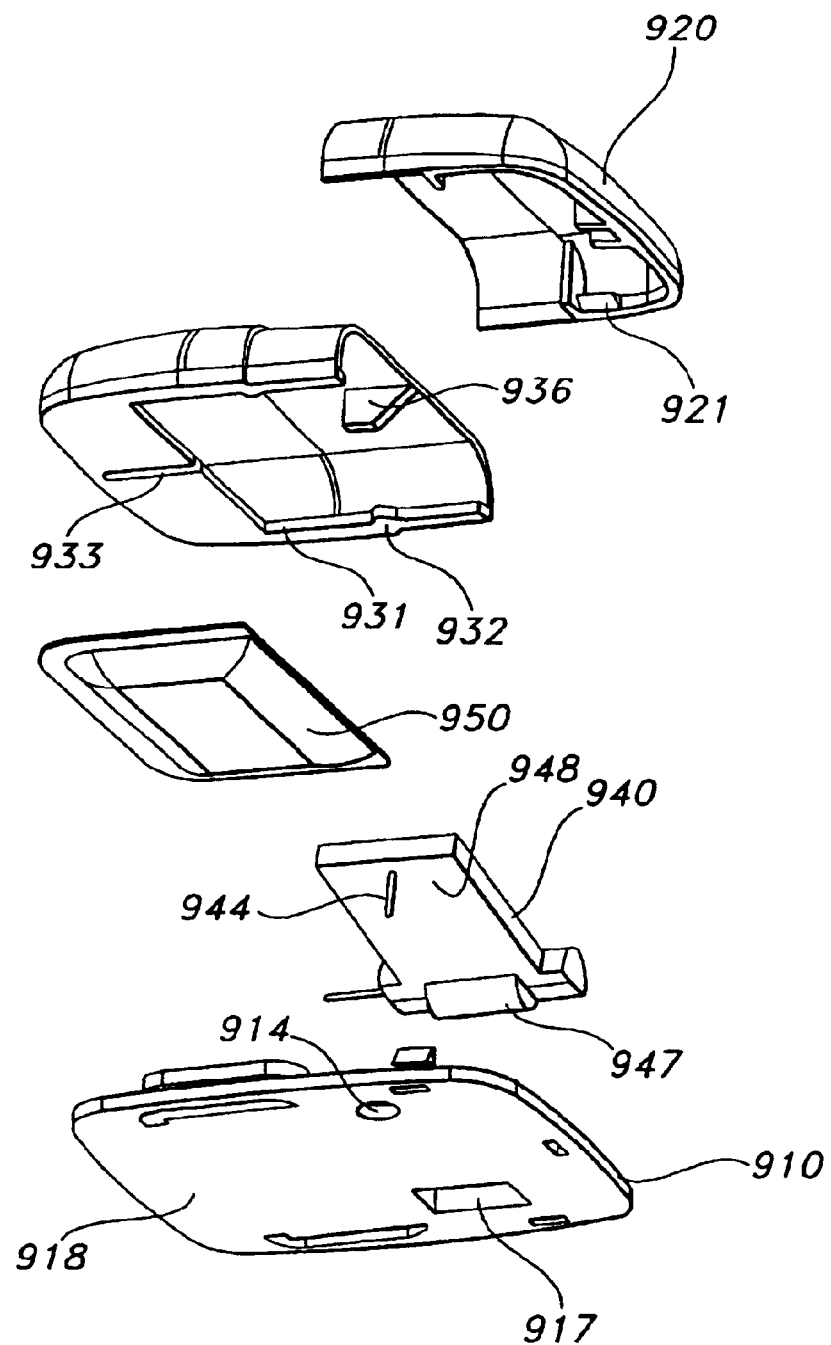
FIG. 9B shows an exploded view of the drug infusion device seen from below.
Figure 9C:
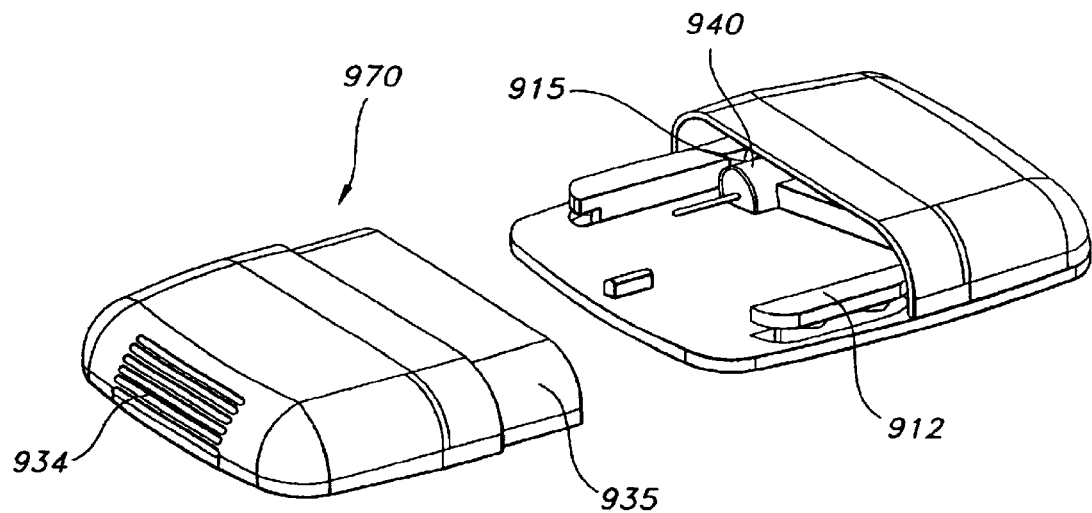
FIGS. 9C and 9D shows the drug infusion device comprising two sub-assemblies.
Figure 9D:
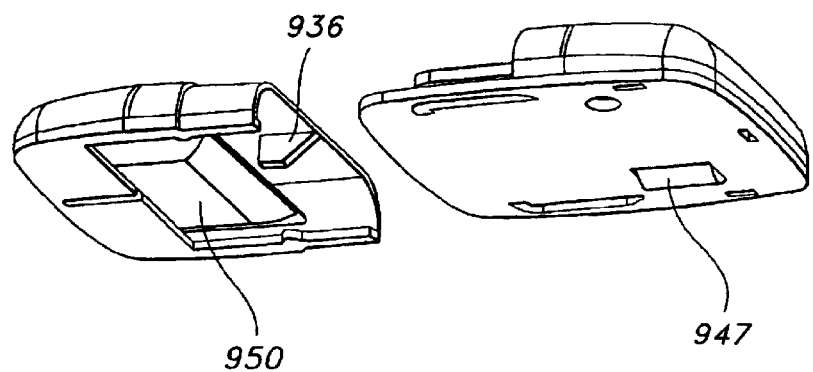
Figure 9E:
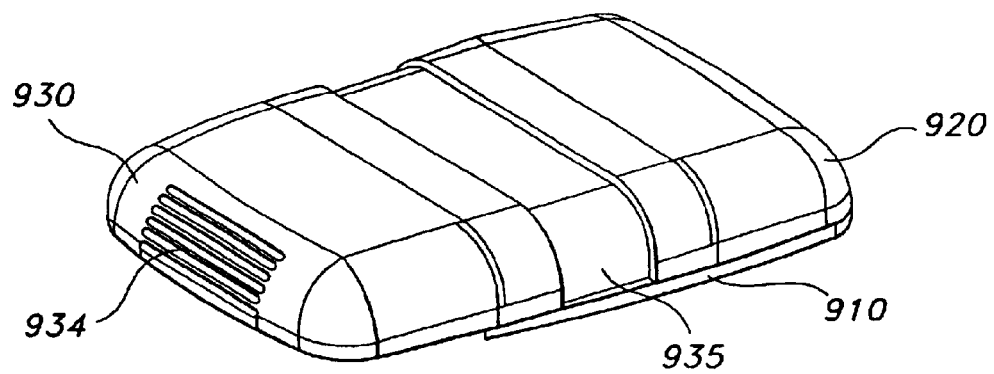
FIG. 9E shows the drug infusion device in an assembled initial state.

The drug infusion device 901 is supplied to the user with the two subassemblies assembled corresponding to an initial state as shown in FIG. 9E. More specifically, the reservoir assembly is mounted in sliding engagement with the base plate member by means of the connecting members 912, 931, a cavity inclosing the reservoir thereby being formed between the second cover member and the base plate member, the reservoir connecting means being arranged in axial alignment with the inlet needle. In the initial state the reservoir assembly is not fully moved towards the first cover member, however, the shroud is partially inserted under the first cover member, this providing a closed cavity. The locking or ratchet means 916, 932 arranged between the second cover member and the base plate member may be configured to prevent that the reservoir assembly can be removed by the user.

Figure 9F:
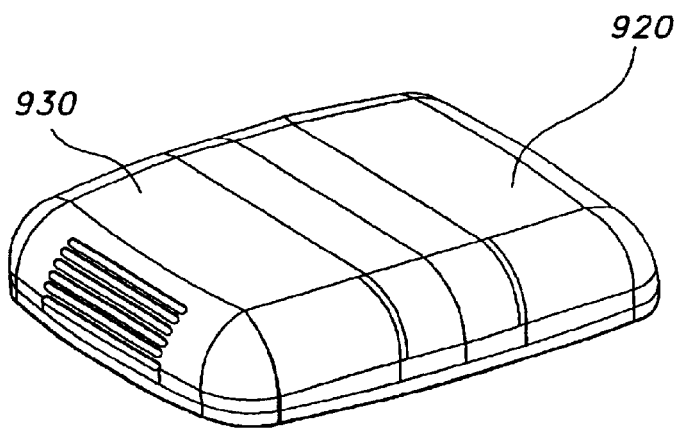
FIG. 9F shows the drug infusion device in an assembled actuated state.

To activate the infusion device, the reservoir assembly is moved towards the pump assembly (see FIG. 9F) whereby a number of actions takes place. More specifically, the inlet needle 943 will penetrate the reservoir connecting means providing fluid communication between the reservoir and the pump, and the ramp 936 on the second cover member will engage the pump assembly to thereby pivot it downwardly whereby the infusion needle 944 will be moved through the aperture 914. At the same time contact means arranged on the pump assembly (e.g. on the lower surface of the pump body) will be activated, thereby activating the pump control means and eventually the pump, however, the activated control means may be adapted to "wait" for a command signal from an external signal (e.g. supplied from a remote control device) before the pump is actuated. In an alternative embodiment (not shown) the reservoir assembly and the pump assembly may be adapted to move linearly, e.g. in a colinear fashion when arranged in a "stack". In further alternative embodiments (not shown) the reservoir may be connected to the pump, the pump being started, and the needle introduced partly or fully independently of each other, e.g. by two or three user actuated actions.

The drug infusion device 901 may be used in the following way. After the liner has been removed the device is place on a suitable skin portion of the user, e.g. in the abdominal region after which the reservoir assembly serving as a button (indicated by the grooved area 931) is pushed towards the main portion until it locks in place, this, as described above, resulting in activation of the pump and introduction of the needle subcutaneously through the skin of the user. Depending on the programming of the control means, the pump may start to operate immediately or it may wait for user activated commands before pump action is initiated, e.g. commands received from a remote commander or from input means arranged on the device. Before infusion in accordance with a given (basal) infusion rate begins, the pump will advantageously perform a priming action as described above. As the volume of air initially trapped in the infusion pump and the associated conduits (including the two needles) normally is very small, it will in most cases be acceptable to expel this volume of air into the user, however, if this is not desirable, actuation of the infusion device (i.e. pushing the two assemblies together) will have to be performed before the device is mounted on the skin.

When the device is to be removed, it may be pulled off the skin in its active state with the needle protruding from the lower surface, or the device may be reversed to its initial state before it is removed. For example, if locking means are arranged between the shroud and the first cover member, the locking means may be released by pushing down the upper surface of the first cover member.

In the above description of the exemplary embodiments, the different structures providing mechanical and electrical contact and communication between the different components just as the means providing the described functionality for the different components (i.e. dose setting, reservoir, energy source, memory, control means, display etc.) have been described to a degree to which the concept of the present invention will be apparent to the skilled reader. The detailed construction and specification for the different structures are considered the object of a normal design procedure performed by the skilled person along the lines set out in the present specification.

What is claimed is:

1. A pump device comprising:
    a pump housing,
    a pump cavity formed within the housing, the pump cavity comprising a first wall portion and an opposed second wall portion, the first wall portion having a generally hollow configuration and the second wall portion having a generally raised configuration relative to the pump cavity,
    a pump membrane comprising a first membrane surface and a second membrane surface, the pump membrane being arranged within the pump cavity,
    a pump chamber defined between the first wall portion and the first membrane surface,
    an actuation chamber defined between the second wall portion and the second membrane surface,
    inlet means in fluid communication with the pump chamber,
    outlet means in fluid communication with the pump chamber, wherein
    the pump membrane has a maximum volume position in which the second membrane surface in a stretched state abuts and substantially conforms to the general configuration of the second wall portion, and a drained volume position in which the first membrane surface in a stretched state abuts and substantially conforms to the general configuration of the first wall portion, and
    actuating means for periodically shifting the pump membrane between the maximum volume position and the drained volume position, whereby metering accuracy of the pump device is determined by the first and second wall portions.

2. A pump device as defined in claim 1, wherein the first wall portion has a generally concave configuration and the second wall portion has a generally convex configuration relative to the pump cavity.

3. A pump device as defined in claim 1, wherein the inlet means and the outlet means comprise an inlet valve respectively an outlet valve.

4. A pump device as defined in claim 3, wherein at least one of the valves comprises:
   a valve cavity generally formed from a wall portion and a valve seat portion, the valve seat portion having a generally convex configuration relative to the valve cavity, the valve seat portion comprising a fluid inlet,
   a valve membrane comprising a first valve membrane surface, a second valve membrane surface and a valve opening, the valve membrane being arranged within the valve cavity,
   a valve chamber defined between the first membrane surface and the wall portion, the valve chamber comprising a fluid outlet, wherein
   the valve membrane has a closed position in which the second valve membrane surface in a stretched state abuts and substantially conforms to the general configuration of the valve seat portion thereby closing the fluid inlet, and an open position in which the second valve membrane surface in a further stretched state is at least partially lifted away from the valve seat portion, thereby providing fluid communication between the fluid inlet and the fluid outlet via the valve opening.

5. A pump as defined in claim 3, wherein the pump housing comprises:
   a first housing portion comprising the first wall portion of the pump cavity, and a first portion of at least one of the inlet and outlet valves,
   a second housing portion comprising the second wall portion of the pump cavity, and a second portion of the at least one of the inlet and outlet valves,
   a membrane member disposed between the first and second housing portions forming the pump membrane and the valve membrane for at least one of the inlet and outlet valves arranged between the first and second portions valve(s).

6. A pump device as defined in claim 1, comprising a fluid conduit in flow communication with the actuation chamber, and actuation me for applying a variable fluid pressure in the actuation chamber for periodically shifting the pump membrane between the maximum volume position and the drained volume position, the actuation means being in flow communication with the actuation chamber through the fluid conduit.

7. A pump device as defined in claim 6, wherein the actuation means comprises means for providing a flow of fluid to the actuation chamber through the fluid conduit to thereby shift the pump membrane from the maximum volume position to the drained volume position, and means for controlling a flow of fluid from the actuation chamber through the fluid conduit to thereby shift the pump membrane from the drained volume position to the maximum volume position.

8. A pump device as defined in claim 6, comprising a fluid chamber in fluid communication with the actuation chamber, and heating means associated with the fluid chamber.

9. A pump as defined in claim 4, wherein a fluid chamber in fluid communication with the actuation chamber is formed between the first and second housing portions, heating means being associated with the fluid chamber.

10. A pump device as defined in claim 6, further comprising:
   a transmission cavity including a moveable transmission member arranged there within, the transmission cavity comprising an inlet chamber and an outlet chamber sealed from each other by the transmission member, the outlet chamber being in fluid communication with the actuation chamber,
   a fluid chamber in fluid communication with the inlet chamber, and
   heating means associated with the fluid chamber.

11. A pump device as defined in claim 10, wherein the housing comprises:
   a first housing portion comprising the first wall portion of the pump cavity, first portions of the inlet and outlet means, and a first portion of the transmission cavity,
   a second housing portion comprising the second wall portion of the pump cavity, second portions of the inlet and outlet means, and a second portion of the transmission cavity,
   a membrane structure disposed between the first and second housing portions forming the pump membrane, the inlet and outlet valve membranes, an the transmission member.

12. A pump device as defined in claim 7, wherein the means for providing the flow of fluid to the actuation chamber through the fluid conduit is taken from a group consisting of gas expansion means, gas generating means, and gas pumping means.

13. A pump device as defined in claim 12, wherein the means for controlling the flow of fluid from the actuation chamber through the fluid conduit is taken from a group consisting of gas contraction, gas consumption, gas pumping means and gas dumping means.

14. A pump device as defined in claim 6, wherein the actuation means is hydraulic pump means.

15. A pump device as defined in any of claims 1–4, comprising actuating means taken from a group comprising a piezoelectric member, and an electrostatic means.

16. A pump device as defined in claim 6, further comprising:
   control means for operating the actuation means at a predetermined priming cycle frequency,
   means for detecting a first membrane movement pattern associated with the pumping of a gas or a mixture of gas and liquid,
   the control means being adapted for continuing operation of the pump in accordance with the priming cycle frequency until a second pre-defined pattern associated with the pumping of a liquid is detected, the control means being adapted to terminate pump actuation in response thereto.

17. A pump device as defined in 6, further comprising:
   control means for operating the actuation means at a predetermined priming cycle frequency,
   means for detecting a membrane movement pattern,
   the control means being adapted for continuing operation of the pump in accordance with the priming cycle frequency until the difference between a series of consecutively detected membrane movement patterns are within a predefined range, the control means being adapted to terminate pump actuation in response thereto.

18. A pump device as defined in claim 16, further comprising detecting means arranged on opposed surfaces of the pump membrane and the housing and providing an electrical impedance which is influenced by movement of the pump membrane relative to the housing, and detection means sensitive to the changes in electrical impedance for providing an output signal representative of movement of the pump membrane.

19. A delivery device comprising:

pump means comprising a pump device as defined in claim 1, a reservoir adapted to contain a liquid drug and comprising an outlet means allowing the reservoir in a situation of use to be arranged in fluid communication with the inlet means of the pump device, the reservoir preferably being a prefilled, flexible reservoir, outlet means being adapted to cooperate with or comprising a transcutaneous access means, control means for operating the pump means to expel a drug from the reservoir and out through the outlet means, and energizing means for energizing the pump means and the control means.

20. A delivery device as defined in claim 19, further comprising a mounting surface adapted for application to the skin of a subject.

21. A delivery device as defined in claim 20, wherein the mounting surface comprises mounting means having an adhesive surface.

22. A delivery device as defined in claim 20 or 21, wherein the outlet means comprises a hollow infusion needle communicating, in a situation of use, with the interior of the reservoir.

23. A delivery device as defined in claim 22, wherein the infusion needle comprises a distal pointed end adapted to penetrate the skin of the subject, the infusion needle being moveable between a first position in which the pointed end of the needle is arranged in a retracted position relative to the mounting surface, and a second position in which the pointed end of the needle projects from the mounting surface.

24. A delivery device as defined in claim 23, wherein the infusion needle is mounted on a pump assembly comprising the pump device, the pump assembly being moveable between a first position in which the pointed end of the needle is arranged in a retracted position relative to the mounting surface, and a second position in which the pointed end of the needle projects from the mounting surface.

25. A delivery device as defined in claim 19, wherein the pump means and the reservoir are moveable relative to each other between a first position in which there is no fluid communication between the reservoir and the pump, and a second position in which fluid communication between the reservoir and the pump is established.

26. A drug delivery device as defined in claim 24, wherein movement of the reservoir between a first position and a second position results in movement of the pump assembly between the first position and the second position thereof.

27. A pump device as defined in claim 1, comprising a pump unit and an actuation unit, the pump unit comprising the pump housing, the pump cavity, the pump membrane, the pump chamber, the actuation chamber, the inlet means, and the outlet means, and the actuation unit comprising the actuation means, wherein the units are adapted to be operatively connected to each other.

28. A pump system as defined in claim 27, wherein the pump unit comprises:

a reservoir for, or containing, a drug to be infused and arranged, in a situation of use, in fluid communication with the inlet means, the reservoir preferably being a prefilled, flexible reservoir, and outlet means being adapted to cooperate with or comprising a transcutaneous access means, the actuation unit comprising:

control means for operating the actuation means, the pump system comprising energizing means for energizing the actuation means and the control means.

29. A delivery device as defined in claim 19, further comprising:

indication means, detecting means for detecting an occlusion condition associated with a pre-defined elevated pressure condition in the pump chamber during pump actuation, the detecting means being adapted to actuate the indication means when the occlusion condition is detected, the outlet means being hydraulically rigid such that a partial or full occlusion of the outlet means will result in a substantially unrestricted pressure rise in the outlet means and thereby the pump chamber.

30. A delivery device as defined in claim 29, wherein the outlet means is in the form of a hollow needle comprising a pointed distal end portion adapted to be inserted though the skin of a subject.

31. A delivery device as defined in claim 29, wherein the occlusion condition associated with a pre-defined elevated pressure condition in the pump chamber is selected from the group comprising the conditions: pressure in the pump chamber, pump membrane position or movement, valve membrane position or movement pressure in the outlet means, pressure in gas or hydraulic actuation means, position or movement of mechanical actuation means, current flow in electrically driven actuation means.

* * * * *